(12) United States Patent
Yamane et al.

(10) Patent No.: US 9,710,598 B2
(45) Date of Patent: Jul. 18, 2017

(54) INFORMATION PROCESSOR, IMAGE DATA OPTIMIZATION METHOD AND PROGRAM

(75) Inventors: Kenji Yamane, Kanagawa (JP); Seiji Miyama, Kanagawa (JP); Masato Kajimoto, Chiba (JP)

(73) Assignee: Sony Corporation, Tokyo (JP)

( * ) Notice: Subject to any disclaimer, the term of this patent is extended or adjusted under 35 U.S.C. 154(b) by 384 days.

(21) Appl. No.: 13/325,450

(22) Filed: Dec. 14, 2011

(65) Prior Publication Data

US 2012/0162228 A1 Jun. 28, 2012

(30) Foreign Application Priority Data

Dec. 24, 2010 (JP) .................................. 2010-287247

(51) Int. Cl.
G06F 19/00 (2011.01)
H04N 19/46 (2014.01)
H04N 19/33 (2014.01)

(52) U.S. Cl.
CPC ........... *G06F 19/321* (2013.01); *H04N 19/33* (2014.11); *H04N 19/46* (2014.11)

(58) Field of Classification Search
None
See application file for complete search history.

(56) References Cited

U.S. PATENT DOCUMENTS

| | | | | |
|---|---|---|---|---|
| 5,818,436 A * | 10/1998 | Imai | ..................... | G11B 27/005 |
| | | | | 707/E17.028 |
| 6,031,930 A * | 2/2000 | Bacus | ................ | G01N 15/1475 |
| | | | | 382/133 |
| 6,157,389 A * | 12/2000 | Knowlton | ............. | G06T 3/0012 |
| | | | | 345/660 |
| 7,248,744 B2 * | 7/2007 | Cockshott | ..................... | 382/253 |
| 7,265,786 B2 * | 9/2007 | Venturino et al. | ........ | 348/333.02 |
| 7,738,688 B2 * | 6/2010 | Eichhorn et al. | ............. | 382/133 |
| 8,819,556 B1 * | 8/2014 | Balev | ............................ | 715/723 |
| 2004/0167806 A1 * | 8/2004 | Eichhorn | ............... | G02B 21/26 |
| | | | | 705/3 |
| 2006/0061595 A1 * | 3/2006 | Goede et al. | ................. | 345/619 |
| 2007/0013708 A1 * | 1/2007 | Barcklay et al. | ............. | 345/557 |
| 2009/0028414 A1 * | 1/2009 | Crandall et al. | .............. | 382/133 |
| 2010/0149211 A1 * | 6/2010 | Tossing et al. | ............... | 345/628 |

FOREIGN PATENT DOCUMENTS

| | | |
|---|---|---|
| JP | 2000-148895 A | 5/2000 |
| JP | 2009-037250 A | 2/2009 |

* cited by examiner

*Primary Examiner* — William Beutel
(74) *Attorney, Agent, or Firm* — Chip Law Group

(57) ABSTRACT

Disclosed herein is an information processor including: an image storage section storing a piece of first image data having a first resolution and at least one piece of second image data as layer-by-layer image data for a specimen, the piece of second image data being obtained by spatially compressing the piece of first image data at different magnification ratios; an image data acquisition section acquiring image data from the layer-by-layer image data in units of a predetermined second resolution by which the first resolution is equally divisible to display the image data on a display device; an annotation setting section setting annotations at arbitrary spatial positions of the display image data in response to an instruction from the user; and an image optimization section determining whether each piece of the image data stored in the image storage section is necessary to delete the image data determined to be unnecessary.

7 Claims, 22 Drawing Sheets

F I G . 2
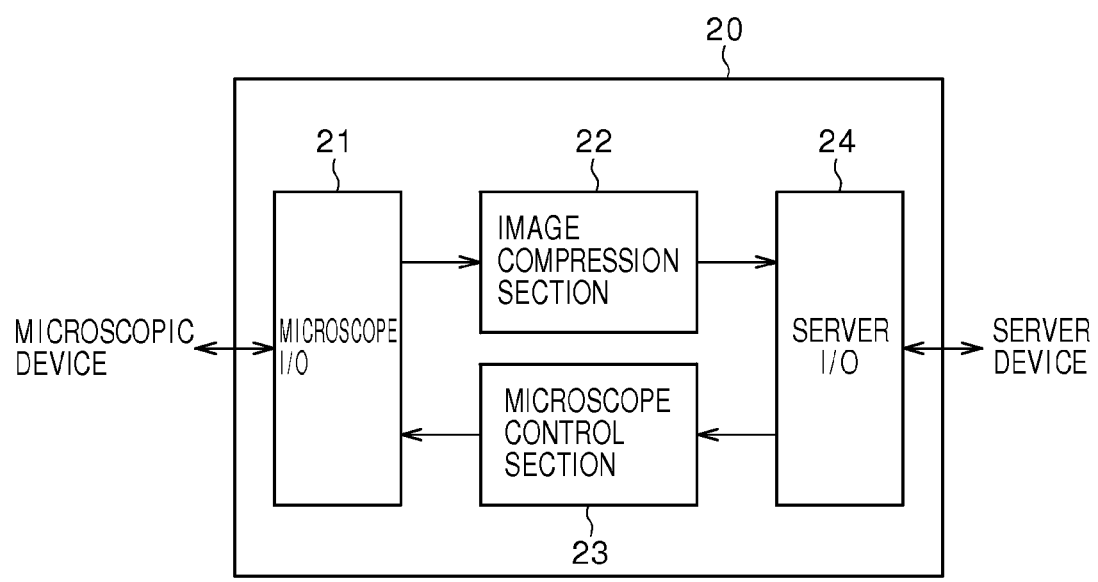

FIG.12
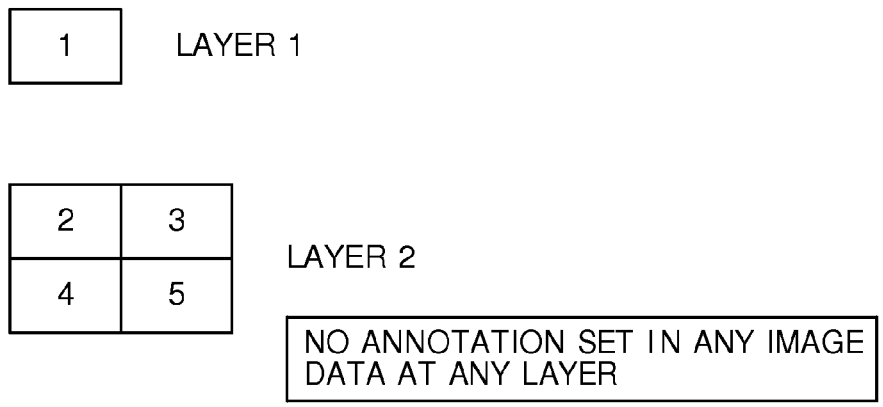
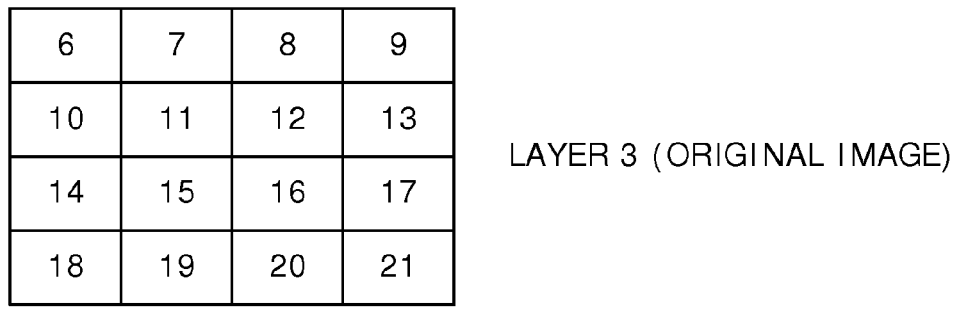
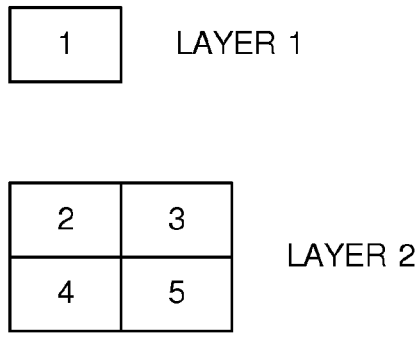
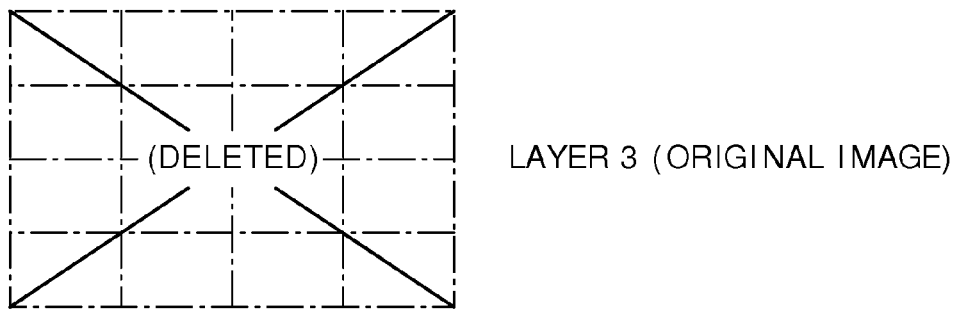

FIG.14
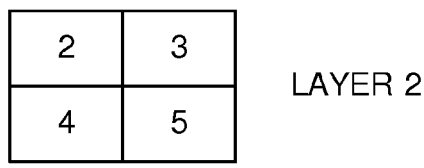
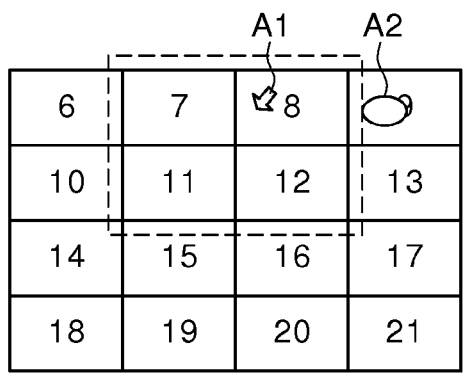
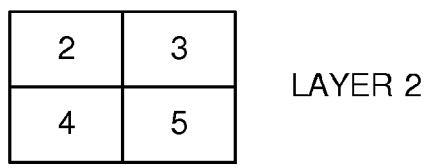
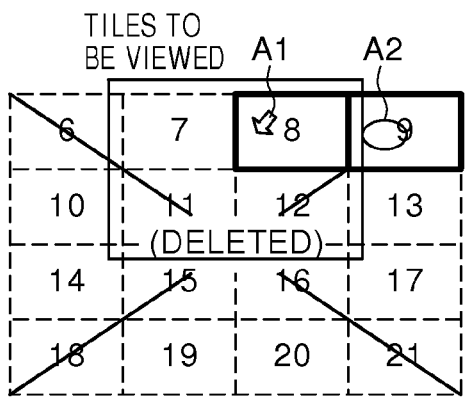

FIG. 16
 LAYER 1
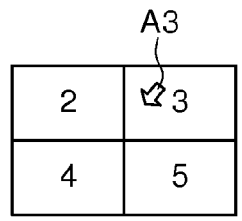 LAYER 2
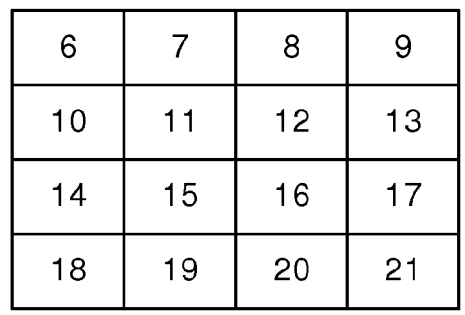 LAYER 3 (ORIGINAL IMAGE)
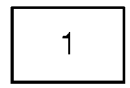 LAYER 1
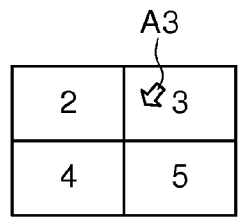 LAYER 2
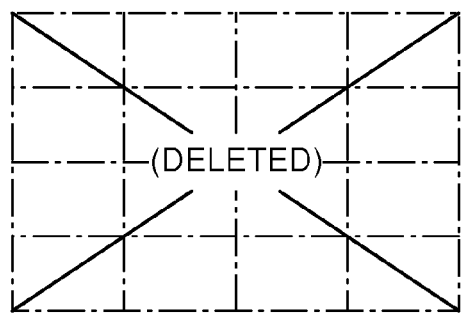 LAYER 3 (ORIGINAL IMAGE)

FIG.18

»annotation type="arrow" …
»slide name="sample_slide"/ …
»position x="1.00" y="2.00"zoomlevel="2"/ …
»/annotation …

INFORMATION PROCESSOR, IMAGE DATA OPTIMIZATION METHOD AND PROGRAM

BACKGROUND

The present disclosure relates to an information processor, image data optimization method and program for accumulating image data and acquiring and displaying the image data in response to an image viewing request from the user.

In medical, pathological and other sectors, a digital pathology technique has been proposed that is designed to digitize an image of a live cell, tissue, organ and so on obtained by an optical microscope so as to allow for medical doctors, pathologists and others to test the tissue and diagnose a patient based on the digital image.

In the method described in Japanese Patent Laid-Open No. 2009-37250 (referred to as Patent Document 1, hereinafter), for example, an image obtained by an optical microscope is digitized by a video camcorder incorporating a CCD (Charge Coupled Device), and the digital signal thereof is fed to a control computer system for visualization on a monitor (refer to paragraphs [0027] and [0028] and FIG. 5 in Patent Document 1).

In the system descried in Japanese Patent Laid-Open No. 2000-148895 (referred to as Patent Document 2, hereinafter), for example, position information is set at an arbitrary location of such an image such as an area suspected by the observer as an ailing bodily part. Content information is associated with this position information. This system displays position information in the form of a mark together with an image and accepts the operation adapted to select the displayed mark using an input device such as a mouse, displaying the content information registered in association therewith (refer to paragraph [0027] and FIG. 5 in Patent Document 2). The function adapted to associate positional and content information with an image and display an image visually combining the positional and content information as described above is referred to as an "annotation function."

SUMMARY

In a microscopic system as described above, a microscopic image of the specimen enlarged at a high magnification ratio is captured using an image sensor such as CCD having an enormous resolution to diagnose the condition of the cellular tissue from the observation image. The captured image (original image) is stored in an 'as-is' fashion. At the same time, images compressed from the original image at magnification ratios of 1/2, $1/2^2$, $1/2^3$ and so on down to $1/2^N$ are generated and stored. The structure in which the images are layered by compressing the original image at different magnification ratios as described above is referred to as an "image pyramid structure." On the other hand, each of the images is managed in units of a predetermined resolution such as about 256 by 256 pixels or 256 by 512 pixels so that a desired tile at a desired magnification ratio can be uniquely selected by specifying its tile ID.

On the other hand, an arrangement has been under study in recent years that is designed to manage, in a unified way, data of the images captured by microscopes using a server device and respond to an image viewing request from a viewer device connected to the server device via a network with necessary image data. Such a system allows for a plurality of observers to access the server device from a plurality of viewer devices at the same time for observation, thus holding promise of providing improved diagnostic efficiency.

However, an image captured by a microscope is enormous in size. Besides, the capacity to store such an image becomes increasingly large because each original image is transformed into an image pyramid structure. Despite a remarkable progress in increasing the capacity of storage devices typified by HDDs (Hard Disc Drives) in recent years, a microscopic system adapted to store information of the order of gigabytes per image capture may result in the replacement of the recording device at relatively short intervals. A possible countermeasure against this problem would be to delete the data of low importance and unnecessary data. However, it is difficult from the viewpoints of cost and work efficiency to artificially manage the data importance so as to determine which data to delete.

In light of the foregoing, it is desirable to provide an information processor, image data optimization method and program for effectively downsizing image data layered at different resolutions without reducing the informativeness of the image data, thus contributing to substantially improved capacity utilization efficiency of the device adapted to store image data and ensuring reduced operation cost.

According to an embodiment of the present disclosure, there is provided an information processor that includes an image storage section, image data acquisition section, annotation setting section and image optimization section. The image storage section stores a piece of first image data having a first resolution and at least one piece of second image data as layer-by-layer image data for a specimen. The piece of second image data is obtained by spatially compressing the piece of first image data at different magnification ratios. The image data acquisition section acquires image data from the layer-by-layer image data stored in the image storage section in units of a predetermined second resolution by which the first resolution is equally divisible so as to display the image data on a display device. The annotation setting section sets annotations at arbitrary spatial positions of the display image data in response to an instruction from the user. The image optimization section determines, based on the set annotations and on a layer-by-layer basis or in units of the second resolution, whether each piece of the image data stored in the image storage section is necessary so as to delete the image data determined to be unnecessary.

In the present disclosure, the piece of first image data having the first resolution and the one or more pieces of second data obtained by spatially compressing the piece of first image data at different magnification ratios make up layer-by-layer image data for a specimen. The image storage section adapted to store image data layered at different resolutions diminishes in its capacity as image data of specimens is stored one after another. In the present disclosure, the image optimization section determines, based on the annotations set in the image data in response to an instruction from the user on a layer-by-layer basis or in units of the second resolution, whether layer-by-layer image data for a specimen is necessary so as to delete the image data determined to be unnecessary. Here, an image data with an annotation is that which drew attention of the image observer at least once. Therefore, it can be said that this data is highly valuable in terms of informativeness. Therefore, this data is excluded from data subject to deletion for optimization. In contrast, it can be said that image data with no annotation is relatively low in value in terms of informativeness. Therefore, this data is subject to deletion for optimization. Also, an annotation is set at an arbitrary spatial position of image data. Therefore, the image optimization section can determine, on a layer-by-layer basis or in units of the second resolution, whether image data is necessary so as to delete unnecessary data. Therefore, the present disclosure provides effective downsizing of image data layered at different resolutions without reducing the informativeness of the image data.

An image data optimization method based on another mode of the present disclosure stores, in an image storage section, a piece of first image data having a first resolution and at least one piece of second image data as layer-by-layer image data for a specimen. The piece of second image data is obtained by spatially compressing the piece of first image data at different magnification ratios. The image data optimization method uses an image data acquisition section to acquire image data from the layer-by-layer image data stored in the image storage section in units of a predetermined second resolution by which the first resolution is equally divisible so as to display the image data on a display device. The image data optimization method uses an annotation setting section to set annotations at arbitrary spatial positions of the display image data in response to an instruction from the user. The image data optimization method uses an image optimization section to determine, based on the set annotations and on a layer-by-layer basis or in units of the second resolution, whether each piece of the image data stored in the image storage section is necessary so as to delete the image data determined to be unnecessary.

A program based on still another mode of the present disclosure allows a computer to function as an image storage section, image data acquisition section, annotation setting section and image optimization section. The image storage section stores a piece of first image data having a first resolution and at least one piece of second image data as layer-by-layer image data for a specimen. The piece of second image data is obtained by spatially compressing the piece of first image data at different magnification ratios. The image data acquisition section acquires image data from the layer-by-layer image data stored in the image storage section in units of a predetermined second resolution by which the first resolution is equally divisible so as to display the image data on a display device. The annotation setting section sets annotations at arbitrary spatial positions of the display image data in response to an instruction from the user. The image optimization section determines, based on the set annotations and on a layer-by-layer basis or in units of the second resolution, whether each piece of the image data stored in the image storage section is necessary so as to delete the image data determined to be unnecessary.

The present disclosure effectively downsizes image data layered at different resolutions without reducing the informativeness of the image data so as to provide substantially improved capacity utilization efficiency of the device adapted to store image data and ensuring reduced operation cost.

BRIEF DESCRIPTION OF THE DRAWINGS

FIG. 2 is a block diagram illustrating the configuration of a control device shown in FIG. 1;

FIG. 12 is a diagram illustrating an example of optimization using the first method;

FIG. 14 is a diagram illustrating an example of optimization using the second method;

FIG. 16 is a diagram illustrating an example of optimization using the third method;

FIG. 18 is a diagram illustrating an example of description of annotation data with XML;

DETAILED DESCRIPTION OF THE PREFERRED EMBODIMENTS

A description will be given below of the preferred embodiments of the present disclosure with reference to the accompanying drawings.

First Embodiment

The present embodiment relates to a microscopic system that includes a microscopic device adapted to capture enlarged images of specimens, a server device adapted to digitize and accumulate the images captured by the microscopic device and a viewer device that can download image data accumulated in the server device for viewing purpose.

In the microscopic system as described above, image data groups, one for each specimen, captured by the microscope and accumulated in the server device, are huge, of the order of gigabytes in size. As a result, the storage capacity of the server device is quickly consumed as a result of repetition of image captures. This has led to much time and effort spent on maintenance including the replacement of the storage at short intervals and the transfer of data to other recording media. As a result, the operation cost tends to increase. Therefore, an arrangement is sought in which the frequency of the storage replacement and data transfer can be kept to a minimum by deleting image data of low importance of all the image data stored in the storage for optimization.

In the present embodiment, an "annotation" set in image data is used as an indicator adapted to represent the degree of importance of image data. The term "annotation" refers to information added to image data as a comment. The annotation is so called to mean not only this information but also attribute representing the presence of a comment or content of the comment. The image data accumulated in the server device is accessed by the viewer device for observation by the observer. At this time, an annotation is set as appropriate at an area (spatial position) of interest in the image recognized by the observer. In an application where a pathological specimen image is observed for diagnosis, for example, a plurality of observers observe the pathological specimen image from their view points to find an area suspected as a lesion part. At this time, the operator of the viewer device, i.e., an observer, sets an annotation at the area suspected as a lesion part. As described above, the setting of an annotation makes it possible to store observation results, thus contributing to significantly improved efficiency in pathological diagnosis.

A description will be given below of the microscopic system capable of optimizing image data by using annotations.

[Configuration of the Microscopic System]

Figure 1:
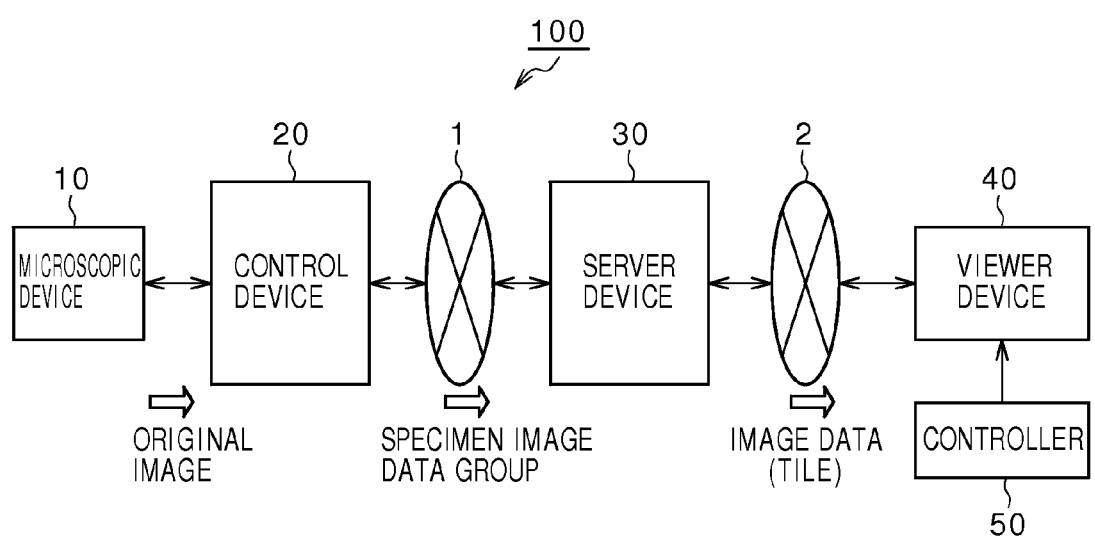
FIG. 1 is a diagram illustrating the overall structure of a microscopic system according to a first embodiment of the present disclosure.

FIG. 1 is a diagram illustrating the overall structure of the microscopic system according to a first embodiment of the present disclosure. As illustrated in FIG. 1, a microscopic system 100 includes a microscopic device 10, control device 20, server device 30 and viewer device 40.

The microscopic device 10 enlarges a specimen image with its magnifying optical system and forms an image on the imaging surface of a CCD (Charge Coupled Device) image sensor, CMOS (Complementary Metal Oxide Semiconductor Image Sensor) image sensor or other imaging element, converting the image into an electric signal, digitizing the signal and transmitting the digital signal to the control device 20.

The control device 20 is connected to the microscopic device 10 via a signal line, supplying a variety of control signals to and receiving image data from the microscopic device 10 via this signal line. The control device 20 codes the image data obtained from the microscopic device 10, uploading the coded image data to the server device 30 via a first network 1 such as a local area network. It should be noted that the control device 20 may be an ordinary PC (Personal Computer).

The server device 30 is connectable to the control device 20 via the first network 1, accumulating the image data uploaded from the control device 20 via the first network 1. Further, the server device 30 is connectable to the viewer device 40 via a second network 2 such as a local area network, responding to a request from the viewer device 40 with image data via the second network 2.

The viewer device 40 transmits a request to the server device 30 via the second network 2 to acquire image data, decoding the image data, sent in response from the server device 30 and outputting the decoded image data to the external display device connected to the viewer device 40.

It should be noted that the first and second networks 1 and 2 may be a common network.

[Configuration of the Control Device 20]

FIG. 2 is a block diagram illustrating the configuration of the control device 20.

As illustrated in FIG. 2, the control device 20 includes, for example, a microscope I/O 21, image compression section 22, microscope control section 23 and server I/O 24. The microscope I/O 21 controls the exchange of various data with the microscopic device 10. The image compression section 22 generates an image pyramid structure from an original image supplied from the microscope I/O 21, compression-coding layer-by-layer image data in a pyramid structure in units of a predetermined resolution (predetermined second resolution by which the first resolution is equally divisible) (in units of the tile). A description will be given later of the image pyramid structure. Among image compression coding schemes that can be used are JPEG (Joint Photographic Experts Group) and JPEG 2000. The microscope control section 23 controls the imaging operation performed by the stage, imaging section and other sections of the microscopic device 10. The server I/O 24 controls the exchange of various data with the server device 30.

[Operation of the Control Device 20]

Figure 7:
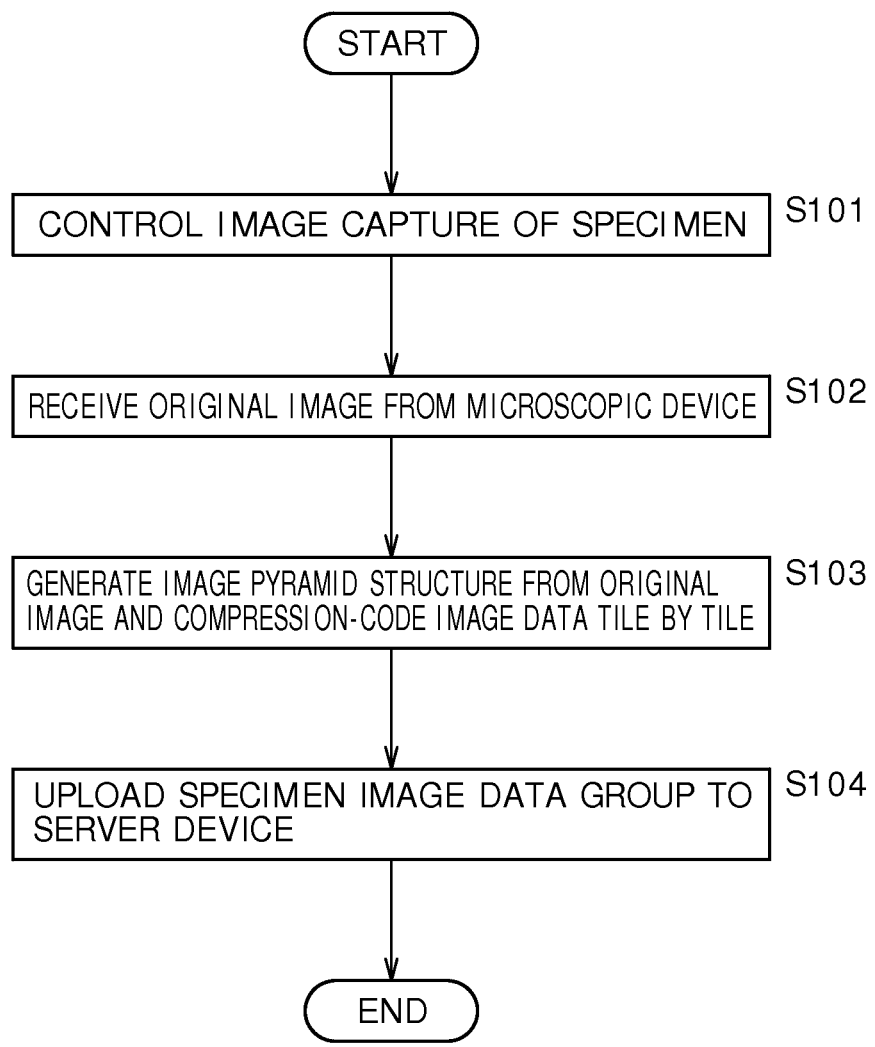
FIG. 7 is a flowchart illustrating the operation of the control device shown in FIG. 2.

FIG. 7 is a flowchart illustrating the operation of the control device 20.

The control device 20 controls the stage, imaging section and other sections of the microscopic device 10 using the microscope control section 23, thus allowing for an image of the specimen to be captured (step S101). As a result, the original image of the specimen is transmitted from the microscopic device 10 to the control device 20 (step S102). The image compression section 22 of the control device 20 generates an image pyramid structure from the original image acquired from the microscopic device 10, compression-coding layer-by-layer image data in the pyramid structure in units of the tile (step S103). Compression-coded layer-by-layer image data obtained from a single specimen as described above will be hereinafter referred to as a "specimen image data group." The specimen image data group is uploaded into the server device 30 via the server I/O 24 and stored in the image data storage of the server device 30 in association with the specimen title (step S104).

It should be noted that the ID (slide title) marked on a slide glass may be used as a title adapted to identify the specimen image data group if the specimen placed on the slide glass and covered with a cover glass is observed.

[Structure of the Specimen Image Data Group]

The image compression section 22 of the control device 20 spatially compresses an original image, obtained from a specimen, at magnification ratios of 1/2, $1/2^2$, $1/2^3$ and so on down to $1/2^N$. This provides (N+1) layers of image data for a specimen. The structure in which images including the original image are layered as a result of the compression of the original image at different magnification ratios as described above is referred to as an "image pyramid structure."

Further, layer-by-layer image data is managed in units of a predetermined resolution by which the resolution of the original image is equally divisible. This unit is the above-described tile. The resolution of the tile is, for example, 256 by 256 pixels or 256 by 512 pixels. A tile ID is assigned to each of the tiles so that the tiles are individually identifiable in the image pyramid structure. This makes it possible for the viewer device 40 to uniquely specify, using a combination of a specimen title and tile ID, information necessary to change the layer position of the image to be displayed (change the zoom factor) or the position of the image to be displayed. Further, the server device 30 can uniquely identify the appropriate tile from the image data storage based on the combination of a specimen title and tile ID. This contributes to fast response from the viewpoint of the viewer device 40.

Figure 5:
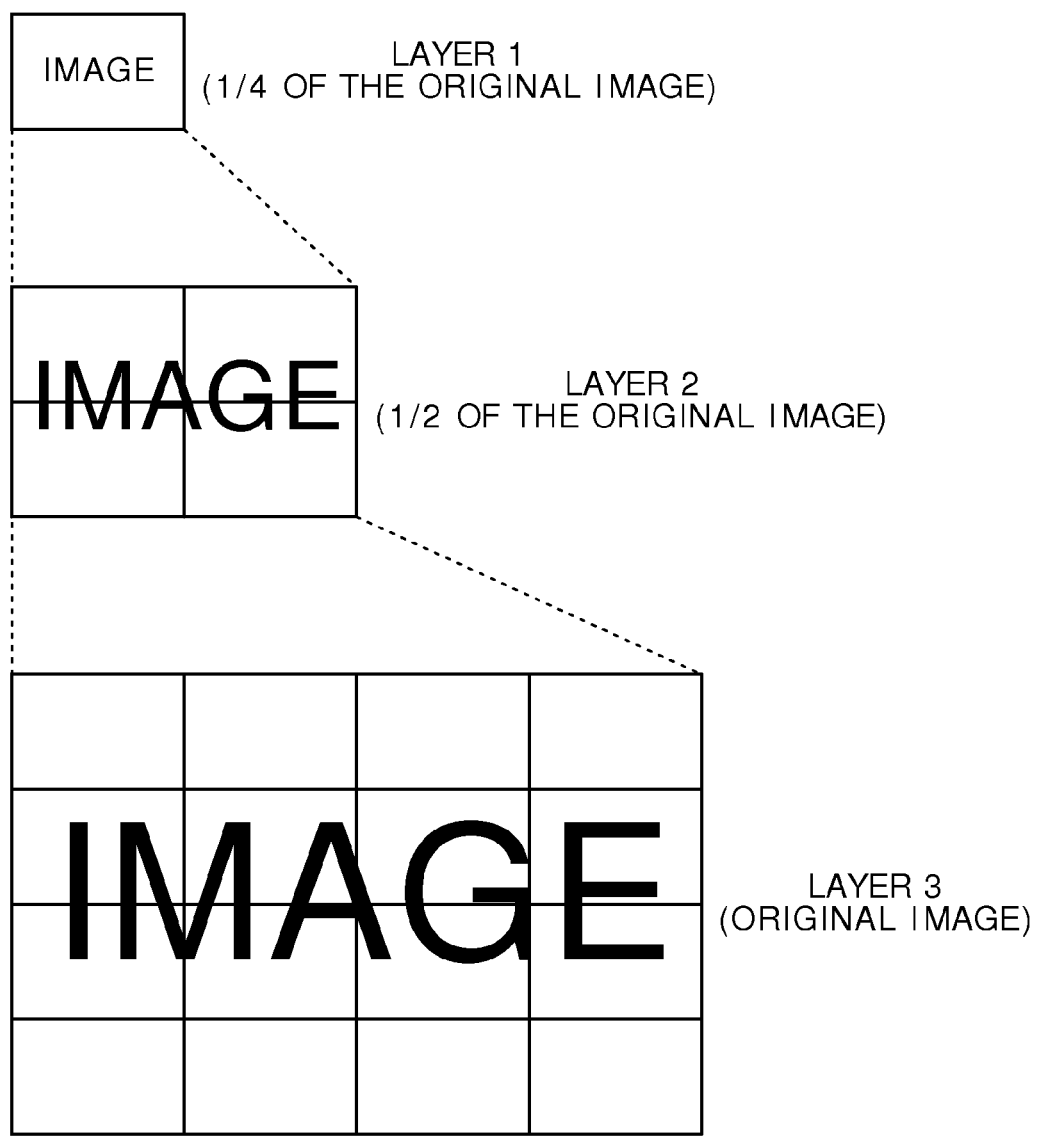
FIG. 5 is a diagram illustrating an example of a compression method of a microscopic image.

FIG. 5 is a diagram illustrating an example of a compression method of an original image.

Figure 6:
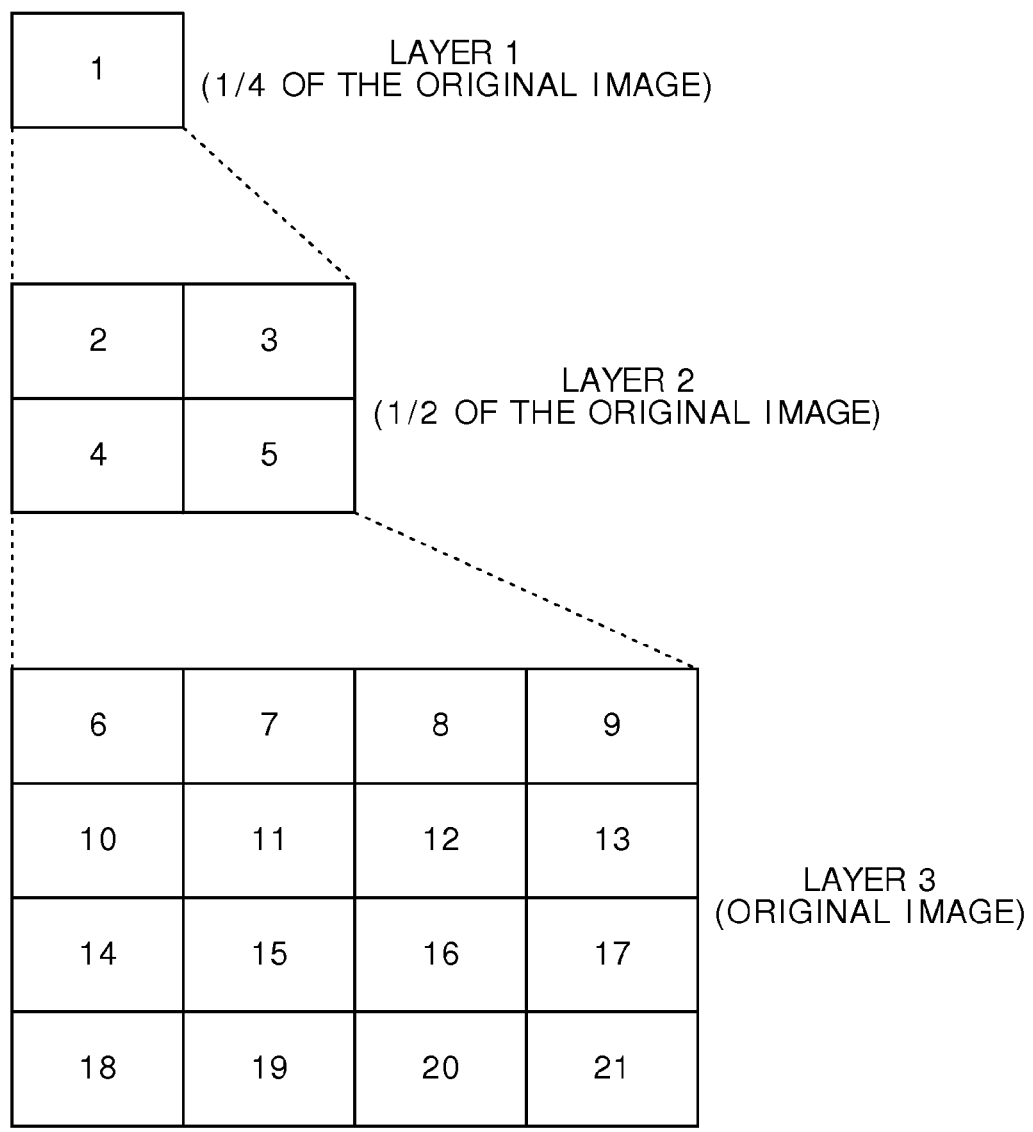
FIG. 6 is a diagram illustrating an example of assignment of an ID to each of tiles in an image pyramid structure.

To simplify the description, we assume in this example that the number of layers is three and that the original image includes a group of four tiles down by four across or 16 tiles. In this case, the image obtained by compressing the original one at a magnification ratio of 1/2 includes a group of two tiles down by two across or four tiles. The image obtained by compressing the original one at a magnification ratio of $1/2^2$ includes a tile. Practically, however, there are more than three layers. FIG. 6 is a diagram illustrating an example of assignment of an ID to each of the tiles. The assignment of a unique ID to each of the tiles as described above allows for each tile to be uniquely specified with its tile ID. Further, it is possible to readily learn about the spatial correspondence between the tiles of different layers. The term "the spatial correspondence between the tiles of different layers" refers to the fact that the tiles are located at a common spatial position. It can be said, for example, that, in FIG. 6, the tile with a tile ID of '4' in layer 2 spatially corresponds to the four tiles with tile IDs of '14,' '15,' '18' and '19' in layer 3 (original image).

[Configuration of the Server Device 30]

Figure 3:
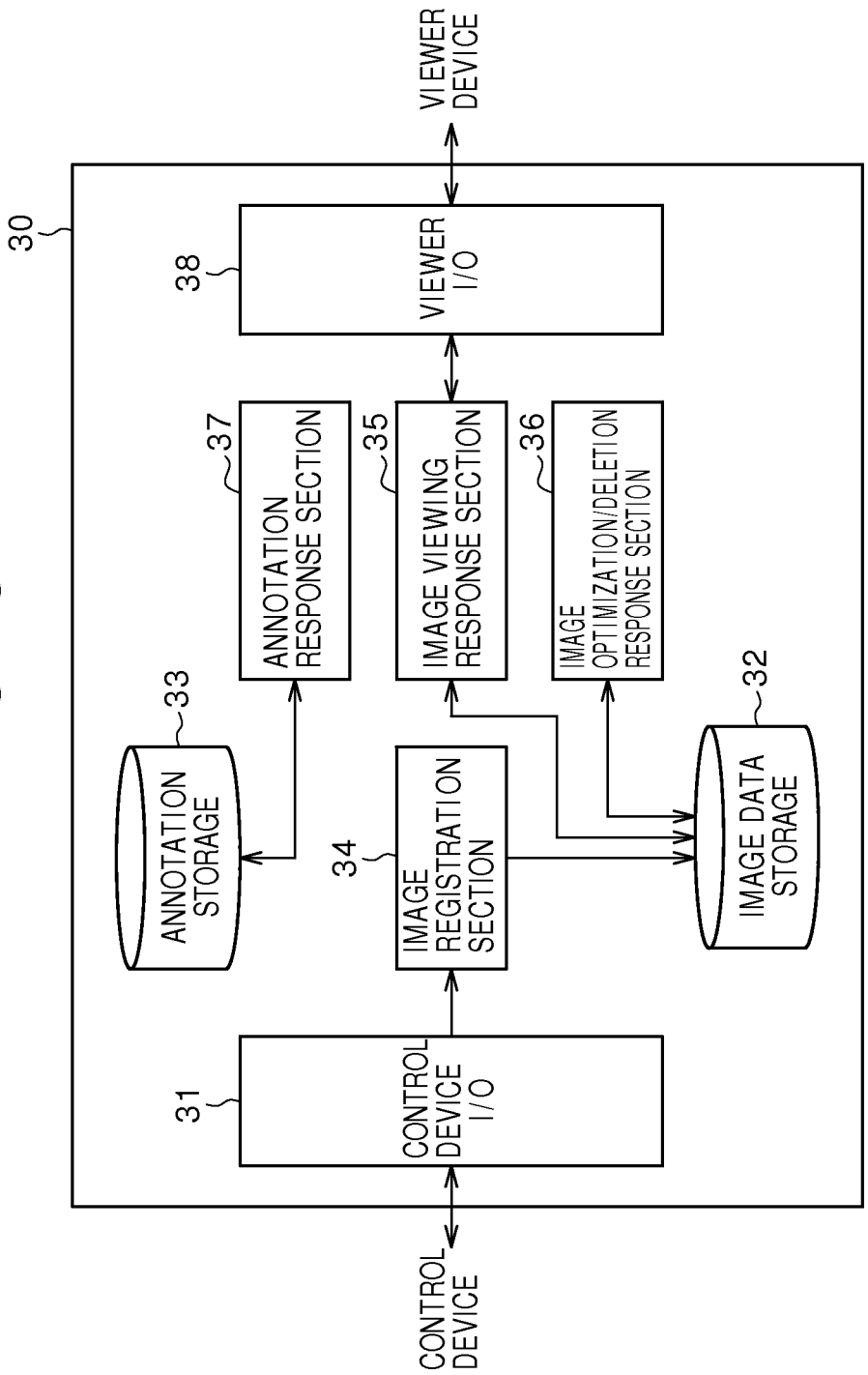
FIG. 3 is a block diagram illustrating a server device shown in FIG. 1.

FIG. 3 is a block diagram illustrating the server device 30.

As illustrated in FIG. 3, the server device 30 includes a control device I/O 31, image data storage 32 (image storage section), annotation storage 33, image registration section 34, image viewing response section 35 (part of the image data acquisition section), image optimization/deletion response section 36 (image optimization section), annotation response section 37 (part of the annotation setting section) and viewer I/O 38.

The control device I/O 31 controls the exchange of various data with the control device 20. The image data storage 32 is a random-access storage section adapted to store specimen image data groups in association with specimen titles. The annotation storage 33 is a storage section adapted to store data of annotations set in specimen image data groups.

Figure 8:
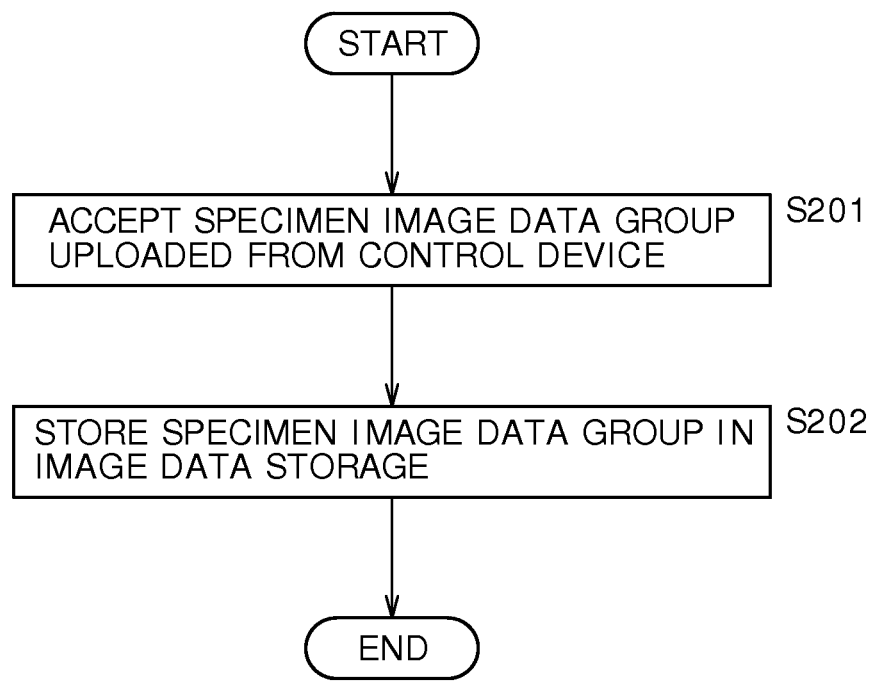
FIG. 8 is a flowchart illustrating the operation of an image registration section of the server device shown in FIG. 3.

The image registration section 34 accepts a specimen image data group uploaded from the control device 20 via the control device I/O 31 as illustrated in FIG. 8 (step S201). The same section 34 stores the accepted specimen image data group in the image data storage 32 in association with the specimen title (step S202). Then, the image registration section 34 generates meta data such as the number of layers of the specimen image data group and the resolution of the original image, registering the meta data in the image meta data storage (not shown) in association with the specimen title.

The viewer I/O 38 controls the exchange of various data with the viewer device 40.

Figure 9:
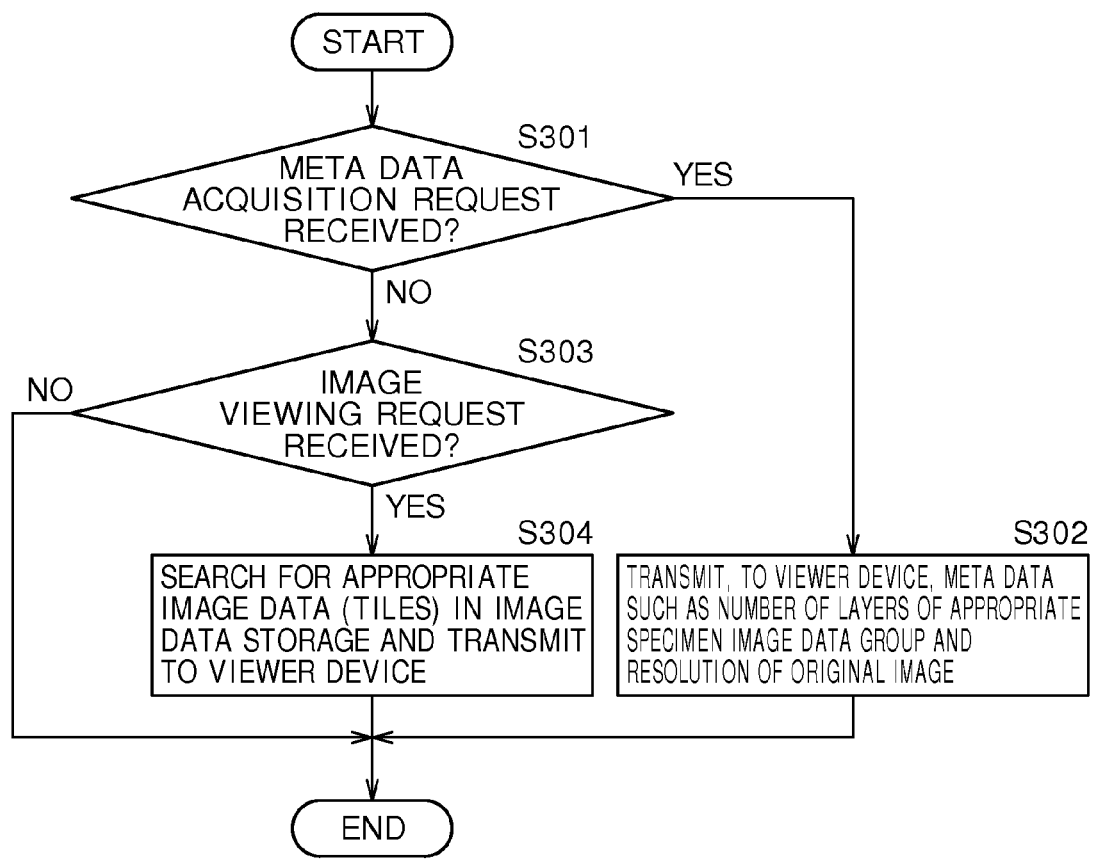
FIG. 9 is a flowchart illustrating the operation of an image viewing response section of the server device shown in FIG. 3.

The image viewing response section 35 accepts and responds to a meta data acquisition request including a specimen title or an image viewing request including a specimen title and tile ID from the viewer device 40. That is, when the image viewing response section 35 receives a request from the viewer device 40 to acquire meta data including a specimen title (Yes in step S301) as illustrated in FIG. 9, the same section 35 reads the meta data about the specimen image data group in question from the image meta data storage (not shown) based on the specimen title, transmitting the meta data to the viewer device 40 via the viewer I/O 38 (step S302). The viewer device 40 can recognize the image pyramid structure of the specimen image data group based on the acquired meta data. This makes it possible for the viewer device 40 to calculate the title ID adapted to identify the image data, i.e., the ID necessary for changing the layer position of the image to be displayed (changing the zoom factor) or the position of the image to be displayed. Further, if an image viewing request including a specimen title and tile ID is received from the viewer device 40 (Yes in step S303), the image viewing response section 35 searches for the appropriate image data (tile) in the image data storage 32 based on the specimen title and tile ID included in the image viewing request, transmitting the image data to the viewer device 40 via the viewer I/O 38 (step S304).

Figure 10:
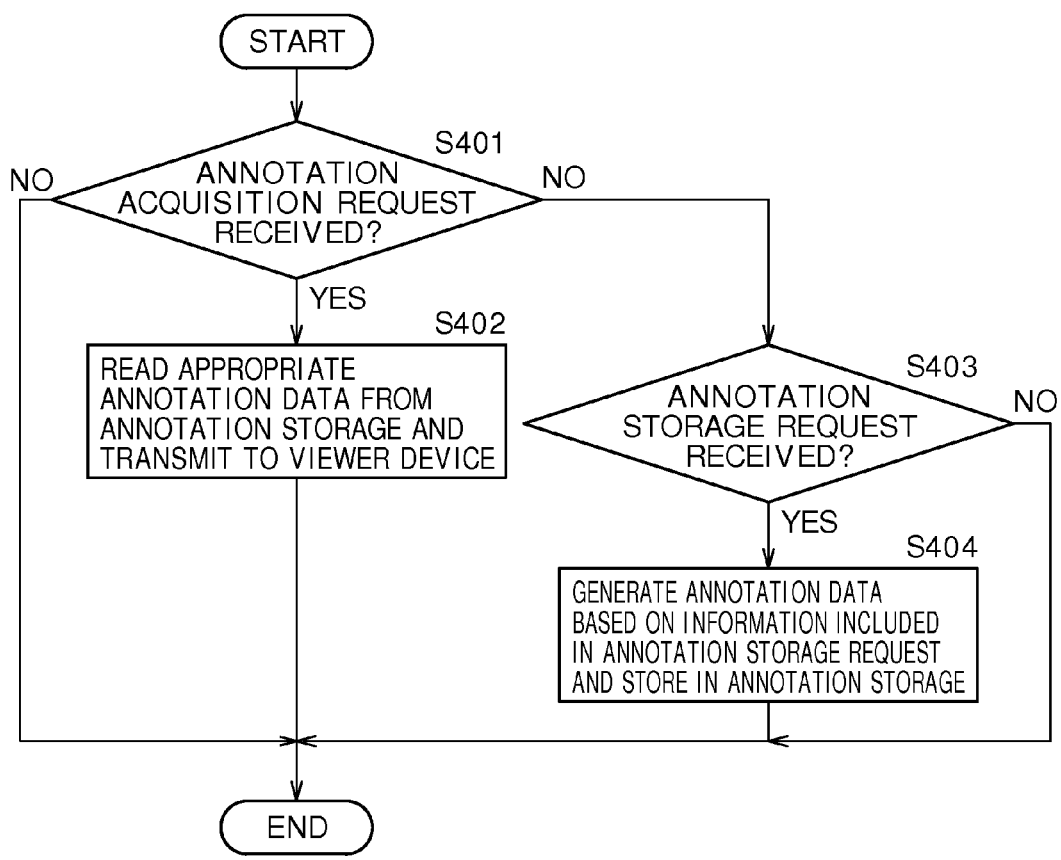
FIG. 10 is a flowchart illustrating the operation of an annotation response section of the server device shown in FIG. 3.

The annotation response section 37 accepts and responds to annotation storage and acquisition requests from the viewer device 40. That is, when the annotation response section 37 receives an annotation storage request from the viewer device 40 as illustrated in FIG. 10 (Yes in step S403), the same section 37 generates annotation data based on the information included in the annotation storage request, registering the annotation data in the annotation storage 33 in association with the specimen title (step S404). Information included in the annotation storage request is a specimen title and image position information. Among pieces of image position information are the layer position of the image and the position of the image of the layer in question in the coordinate space. When the annotation response section 37 receives an annotation acquisition request from the viewer device 40 (Yes in step S401), the same section 37 reads the annotation data, associated with the specimen title included in the annotation acquisition request (specimen title of the image being viewed on the viewer device 40), from the annotation storage 33, responding to the viewer device 40 via the viewer I/O 38 (step S402).

When the image optimization/deletion response section 36 receives an optimization request from the viewer device 40, the same section 36 determines the image data of low importance on a tile-by-tile or layer-by-layer basis based on the annotation data associated with the specimen title included in the optimization request, thus deleting the pieces of image data of low importance for optimization of the specimen image data groups stored in the image data storage 32. The specimen image data groups stored in the image data storage 32 will be hereinafter referred to as the "specimen image data groups." A detailed description will be given later of the optimization of the specimen image data groups.

On the other hand, when the image optimization/deletion response section 36 receives a deletion request from the viewer device 40, the same section 36 deletes the appropriate specimen image data group from the image data storage 32 or the appropriate annotation data from the annotation storage 33 based on the specimen title included in the deletion request.

[Configuration of the Viewer Device 40]

Figure 4:
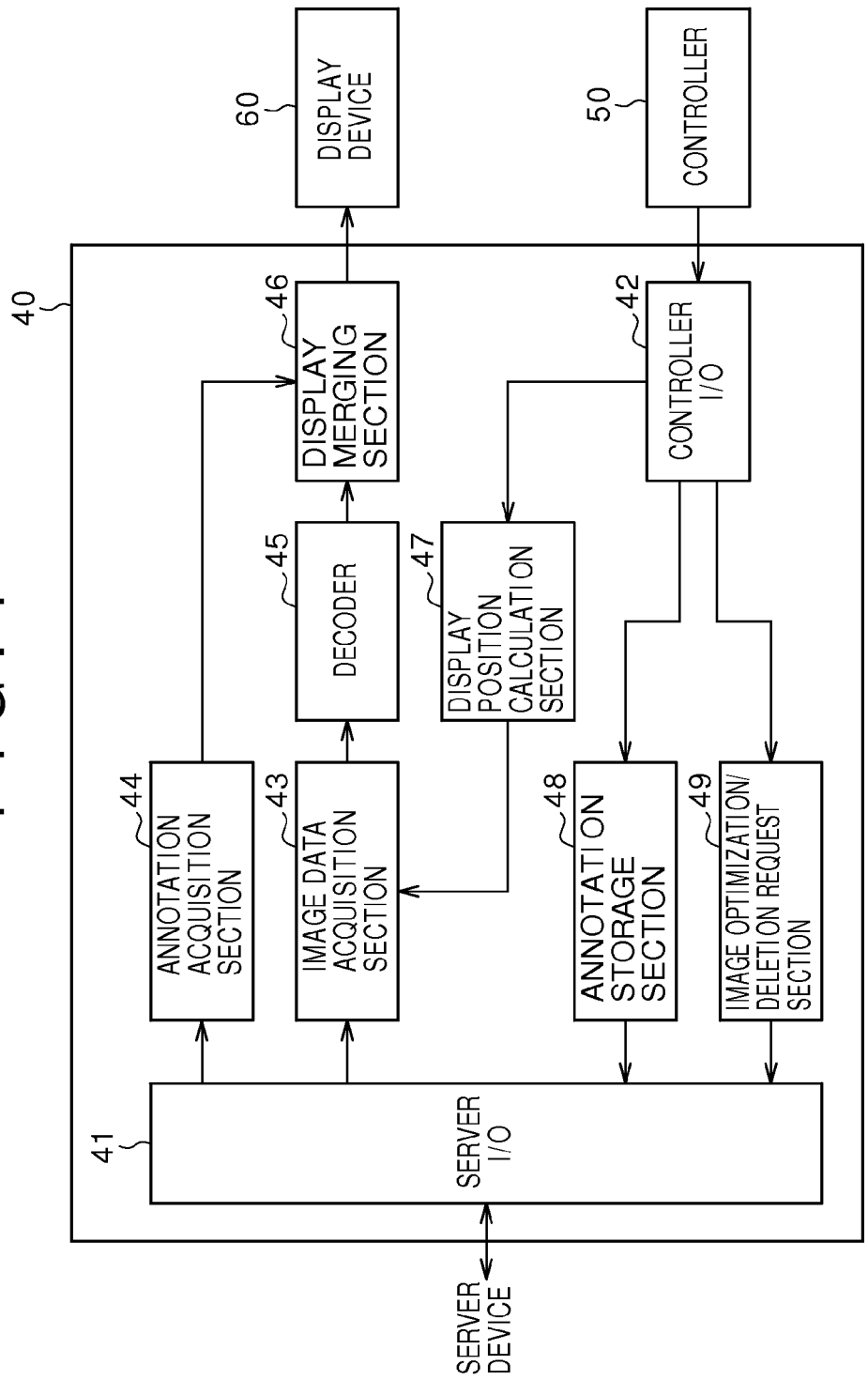
FIG. 4 is a block diagram illustrating the configuration of a viewer device shown in FIG. 1.

FIG. 4 is a block diagram illustrating the configuration of the viewer device 40.

As illustrated in FIG. 4, the viewer device 40 includes, for example, a server I/O 41, controller I/O 42, image data acquisition section 43 (image data acquisition section), annotation acquisition section 44, decoder 45, display merging section 46 (dummy tile generation section), display position calculation section 47, annotation storage section 48 (part of the annotation setting section) and image optimization/deletion request section 49.

The server I/O 41 controls the exchange of various data with the server device 30. The controller I/O 42 is an interface adapted to communicate with a controller 50 manipulated by the user. The controller 50 can accept various instructions and input data from the user.

The user can issue a variety of instructions by manipulating the controller 50 including:

1. Instruction adapted to change the layer position of the image to be displayed (zoom factor change instruction)
2. Instruction adapted to change the spatial position of the image to be displayed
3. Annotation setting instruction
4. Instruction adapted to optimize a specimen image data group
5. Instruction adapted to delete a specimen image data group These instructions are entered, for example, via a GUI (Graphical User Interface) displayed on the screen of a display device 60. The instruction adapted to change the layer position of the image to be displayed (zoom factor change instruction) and the instruction adapted to change the spatial position of the image to be displayed are collectively referred to as the viewpoint change instructions.

The image data acquisition section 43 transmits a meta data acquisition request including a specimen title to the server device 30, thus acquiring meta data about the appropriate specimen image data group from the server device 30. Further, the image data acquisition section 43 can calculate the title ID adapted to identify the image data, i.e., the ID necessary for changing the layer position of the image to be displayed (changing the zoom factor) or the position of the image to be displayed by recognizing the image pyramid structure of the specimen image data group based on the acquired meta data. Then, the image data acquisition section 43 generates an image viewing request including this tile ID and the specimen title and transmits the request to the server device 30 via the server I/O 41, thus acquiring necessary image data (tile) from the server device 30.

The annotation acquisition section 44 transmits an annotation acquisition request including a specimen title to the server device 30 via the server I/O 41, thus acquiring annotation data associated with the specimen title from the server device 30.

The decoder 45 decodes the image data (tile) acquired from the image data acquisition section 43, thus recovering an image in a bitmap format.

The display merging section 46 merges the image in a bitmap format generated by the decoder 45 and the annotation data acquired by the annotation acquisition section 44, thus generating a screen image and outputting the screen image to the display device 60 connected to the viewer device 40.

The display position calculation section 47 calculates the tile ID of the image data to be displayed after the layer position of the image to be displayed (zoom factor) or the position of the image to be displayed is changed by the user, i.e., the observer of the specimen, as a result of the manipulation of the controller 50, thus requesting the image data acquisition section 43 to transmit an image viewing request. The image data acquisition section 43 transmits, in response to this request, an image viewing request including a specimen title and the calculated tile ID to the server device 30 via the server I/O 41.

When supplied with an annotation setting instruction including image position information from the user as a result of the manipulation of the controller 50, the annotation storage section 48 transmits an annotation storage request to the server device 30 via the server I/O 41. An annotation storage request includes a specimen title and image position information. Among pieces of image position information are the layer of the image specified by the user, tile ID and in-tile position.

When supplied with a specimen image data group optimization instruction including image position information from the user as a result of the manipulation of the controller 50, the image optimization/deletion request section 49 transmits an optimization request to the server device 30 via the server I/O 41. Further, when supplied with a specimen image data group deletion instruction from the user as a result of the manipulation of the controller 50, the image optimization/deletion request section 49 transmits a deletion request including the title of the specimen being viewed to the server device 30 via the server I/O 41.

[Zooming In/Out of the Image Display in the Viewer Device 40]

The viewer device 40 supports zooming-in and -out of the image display.

When supplied with a zoom factor change instruction (zooming-in/out instruction) from the user as a result of the manipulation of the controller 50, the display position calculation section 47 calculates the ID of the necessary tile of all the image data of the resolution (layer) associated with the specified zoom factor, requesting the image data acquisition section 43 to acquire the tile with this ID. In response to this request, the image data acquisition section 43 generates an image viewing request including the tile ID and specimen title, transmitting the request to the server device 30 via the server I/O 41 and acquiring the tile from the server device 30. The acquired tile is decoded by the decoder 45 and output to the display device 60 via the display merging section 46. This allows for the zoom factor of the image display to be changed.

Figure 17:
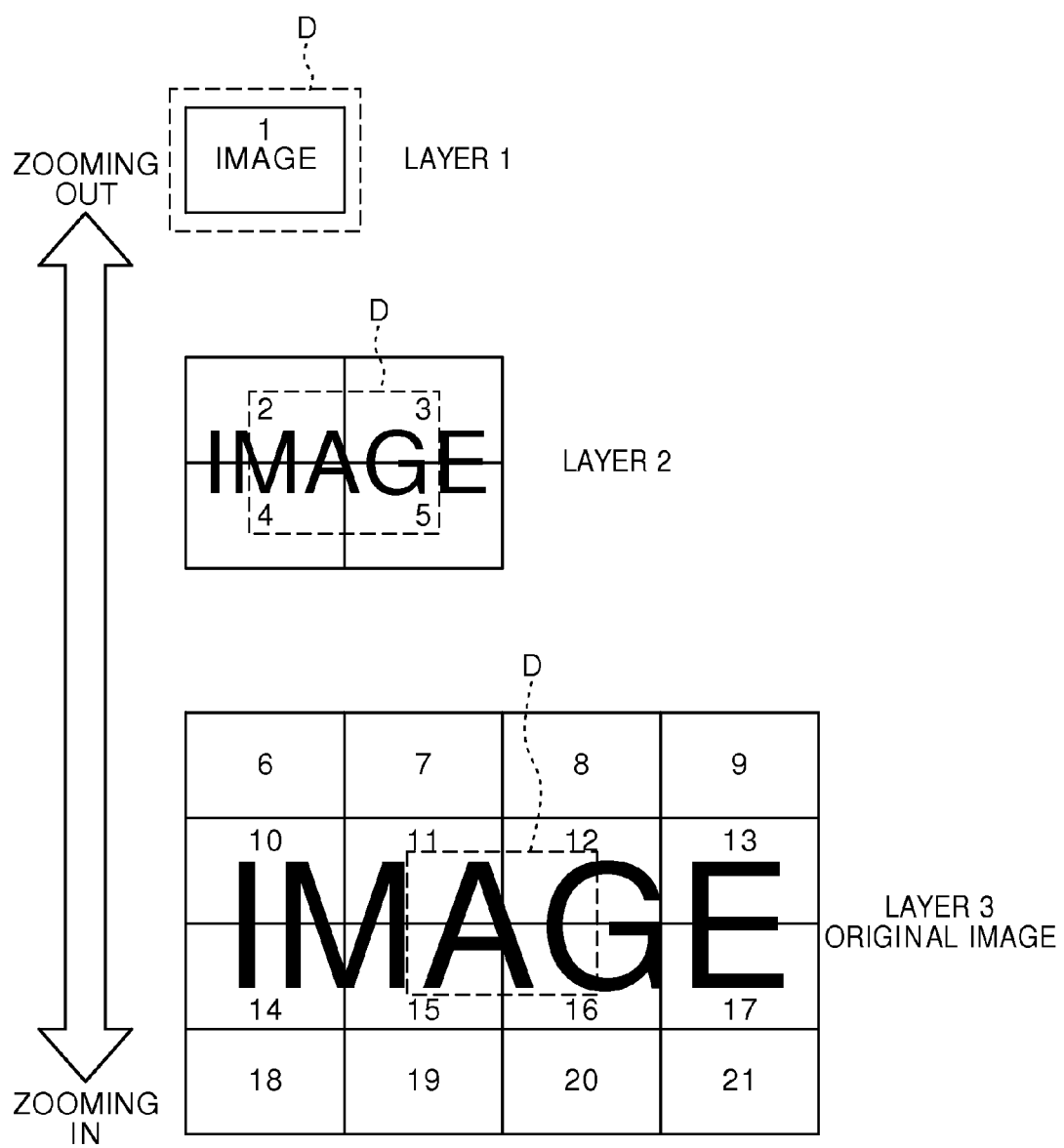
FIG. 17 is a diagram illustrating the relationship between the change in zoom factor and tiles.

FIG. 17 is a diagram illustrating the relationship between the change in zoom factor and tiles.

In FIG. 17, reference numeral D represents the physical screen of the display device 60. When a zooming-in instruction is supplied while the tile in layer 1 (tile ID of 1), obtained by compressing the original image to the resolution of a single tile, is displayed on the physical screen D, the display position calculation section 47 makes calculations to determine that the tiles necessary after the zooming-in are the tiles with IDs of '2,' '3,' '4' and '5' in layer 2. As a result, the image data acquisition section 43 transmits an image viewing request including the tile IDs of '2,' '3,' '4' and '5' to the server device 30, thus acquiring the four tiles and supplying these tiles to the decoder 45. Next, when a zooming-in instruction is supplied again, the display position calculation section 47 makes calculations to determine that the tiles necessary after the zooming-in are the tiles with IDs of '11,' '12,' '15' and '16' in layer 3. As a result, the image data acquisition section 43 transmits an image viewing request including the tile IDs of '11,' '12,' '15' and '16' to the server device 30, thus acquiring the new four tiles and supplying these tiles to the decoder 45.

[Setting and Storage of Annotations]

A description will be given next of the setting and storage of annotations.

An annotation is set, for example, by the observer by manipulating the controller 50 and marking an arbitrary area suspected as a lesion part or enclosing such an area with a line through the screen of the display device 60. Alternatively, it is possible to set an annotation to the layer of the image being displayed. When supplied with an annotation setting instruction from the user, the annotation storage section 48 of the viewer device 40 generates an annotation storage request including, together with a specimen title and layer level information, position information of the marking or enclosing line specified by the user in the coordinate space of the image at that layer level, transmitting the request to the server device 30.

When the annotation response section 37 of the server device 30 receives an annotation storage request from the viewer device 40, the same section 37 generates annotation data based on the information in the annotation storage request and stores the data in the annotation storage 33.

Among pieces of annotation data are the specimen title, the layer with an annotation and the annotation position in the coordinate space of the image at the layer level in question. FIG. 18 illustrates an example of description of annotation data with a markup language such as XML (Extensible Markup Language). With XML, a specimen title can be described as a value of the name attribute of the slide element. Further, an annotation position can be described with values of the x and y attributes of the position element. Still further, an image layer level can be described with a value of the zoomlevel attribute of the position element. It should be noted that the value of the type attribute of the annotation element represents an annotation type. In the example shown in FIG. 18, the annotation type is 'arrow.' This means that the annotation indicates an arbitrary area of the image using an arrow. Using annotation data in such a format makes it possible for the image optimization/deletion response section 36 of the server device 30 to not only uniquely learn about the layer with an annotation but also readily calculate the tile ID including the annotation position in the coordinate space of the image at the layer level in question.

A description will be given next of the operation of the microscopic system 100 according to the present embodiment. The operation of the microscopic system 100 will be described in the following order:

1. Normal image viewing sequence
2. Image viewing sequence including optimization of specimen image data groups
3. Operation for optimization of specimen image data groups
4. Operation for display of the image including the tile deleted for optimization

[1. Normal Image Viewing Sequence]

Figure 19:
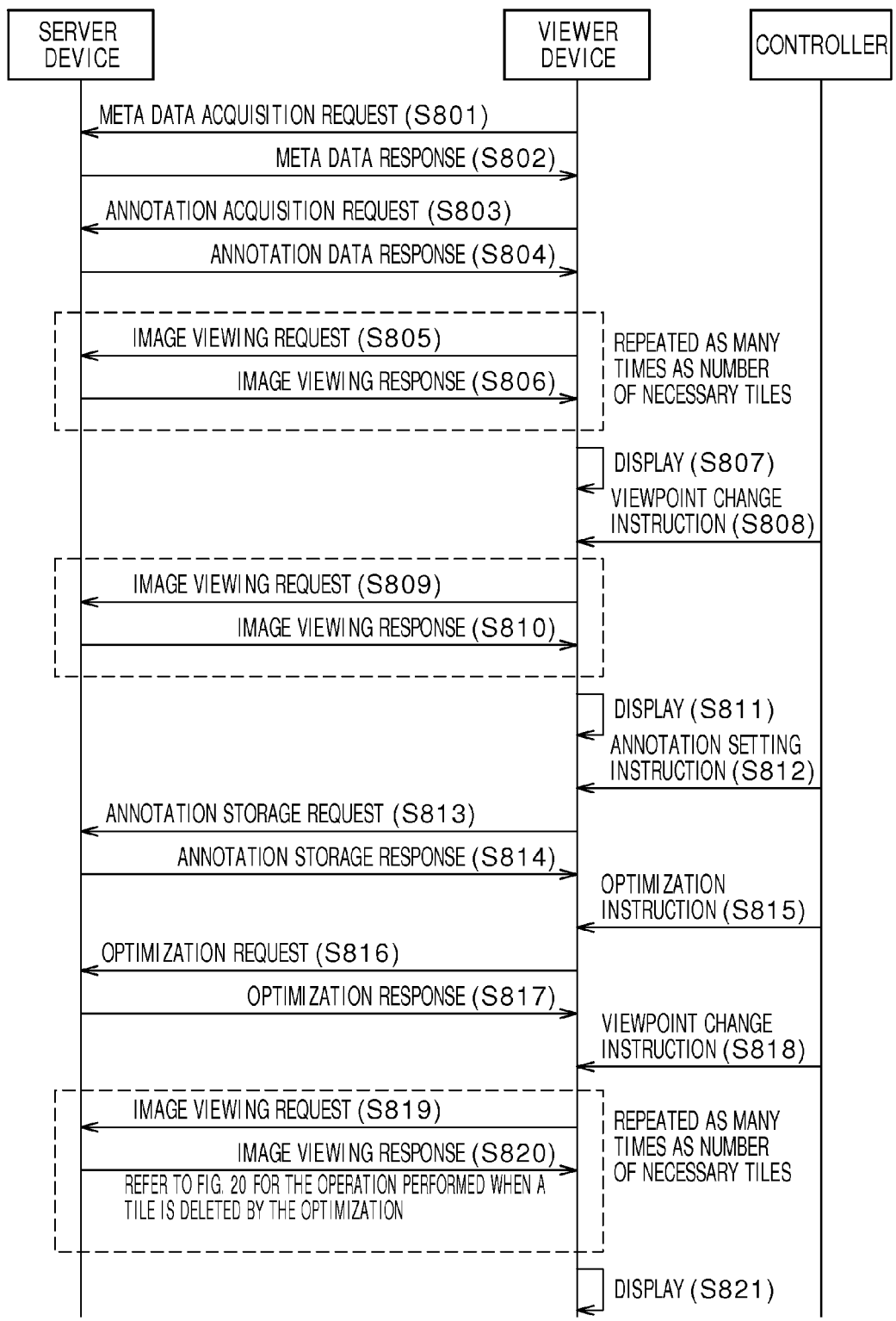
FIG. 19 is a diagram illustrating the image viewing sequence of the microscopic system according to the present embodiment.

FIG. 19 is a diagram illustrating the image viewing sequence of the microscopic system 100 according to the present embodiment.

First, a meta data acquisition request including a specimen title is transmitted from the image data acquisition section 43 of the viewer device 40 to the server device 30 (S801). When the image viewing response section 35 of the server device 30 receives the meta data acquisition request, the same section 35 searches for the meta data relating to the appropriate specimen image data group in the image meta data storage (not shown) based on the specimen title included in the meta data acquisition request and responds to the viewer device 40 (step S802).

Next, an annotation acquisition request including the specimen title is transmitted from the annotation acquisition section 44 of the viewer device 40 to the server device 30 (S803). When the annotation response section 37 of the server device 30 receives the annotation acquisition request from the viewer device 40, the same section 37 searches for the appropriate annotation data in the annotation storage 33 based on the specimen title included in the annotation acquisition request and responds to the viewer device 40 (step S804).

Next, an image viewing request including the specimen title, a default tile ID (e.g., 1) and so on is transmitted from the image data acquisition section 43 of the viewer device 40 to the server device 30 (S805). When the image viewing response section 35 of the server device 30 receives the image viewing request, the same section 35 searches for the appropriate image data (tile) in the image data storage 32 based on the specimen title and tile ID included in the image viewing request and transfers the image data to the viewer device 40 (step S806). The transmission of an image viewing request and the reception of image data are repeated as many times as the number of tiles necessary for the display. The image data (tile) received by the viewer device 40 is decoded by the decoder 45 first, and then merged with necessary annotation data (annotation data set in the tile) by the display merging section 46, and finally supplied to the display device 60. This allows for the first image of the specimen to be viewed to be displayed on the display device 60 (S807).

The user of the viewer device 40 can enter an instruction adapted to change the layer position of the image to be displayed (zoom factor change instruction) or change the position of the image to be displayed as a viewpoint change instruction by manipulating the controller 50. When a viewpoint change instruction is entered from the controller 50 (S808), the display position calculation section 47 calculates the tile ID of the image data to be displayed after the change, thus requesting the image data acquisition section 43 to transmit an image viewing request. In response to this request, the image data acquisition section 43 transmits an image viewing request including the tile ID calculated by the display position calculation section 47 and a specimen title to the server device 30 (step S809). When the image viewing response section 35 of the server device 30 receives the image viewing request from the viewer device 40, the same section 35 similarly searches for the appropriate image data (tile), transferring the image data to the viewer device 40 (S810). The transmission of an image viewing request and the reception of image data (tile) are repeated as many times as the number of tiles necessary for the display. Each piece of the image data received by the viewer device 40 is decoded by the decoder 45 first, and then merged with necessary annotation data (annotation data set in the tile) by the display merging section 46, and finally supplied to the display device 60. This allows for the image of the new viewpoint to be displayed (S811).

[2. Image Viewing Sequence Including Optimization of Specimen Image Data Groups]

A description will be given next of the image viewing sequence including optimization of specimen image data groups with reference to FIG. 19.

The user of the viewer device 40 can enter an annotation setting instruction by manipulating the controller 50 and specifying an arbitrary position of the image of an arbitrary layer displayed on the display device 60. When an annotation setting instruction is entered (S812), the annotation storage section 48 of the viewer device 40 generates an annotation storage request including a specimen title, the specified layer and the position information arbitrarily specified in the image of this layer, transmitting the request to the server device 30 (S813). When the annotation response section 37 of the server device 30 receives the annotation storage request from the viewer device 40, the same section 37 generates annotation data based on the information included in the request, storing the annotation data in the annotation storage 33. When the storage of the annotation data is complete, an annotation storage response is transmitted to the viewer device 40 (S814).

The user of the viewer device 40 can enter, at any time, an instruction adapted to optimize a specimen image data group associated with the specimen image displayed on the display device 60 by manipulating the controller 50. When supplied with the optimization instruction from the user as a result of the manipulation of the controller 50 (S815), the image optimization/deletion request section 49 of the viewer device 40 transmits an optimization request including the specimen title being displayed to the server device 30 via the server I/O 41 (S816). When the image optimization/deletion response section 36 receives the optimization request from the viewer device 40, the same section 36 determines the image data to be deleted on a tile-by-tile or layer-by-layer basis based on the annotation data associated with the specimen title included in the optimization request, thus deleting the piece of image data from the image data storage 32 for optimization of the specimen image data groups. When the optimization of the specimen image data groups is complete, information to this effect is transmitted to the viewer device 40 as an optimization response (S817).

We assume that a viewpoint change instruction is then supplied from the user as a result of the manipulation of the controller 50 in the same manner as described above (S818). The display position calculation section 47 calculates the tile ID of the image data to be displayed after the change based on the viewpoint change instruction, thus requesting the image data acquisition section 43 to transmit an image viewing request. In response to this request, the image data acquisition section 43 transmits an image viewing request including the tile ID calculated by the display position calculation section 47 and a specimen title to the server device 30 (step S819). When the image viewing response section 35 of the server device 30 receives the image viewing request from the viewer device 40, the same section 35 similarly searches for the appropriate image data (tile), transferring the image data to the viewer device 40 (S820). The transmission of an image viewing request and the reception of image data are repeated as many times as the number of tiles necessary for the display. Each piece of the image data received by the viewer device 40 is decoded by the decoder 45 first, and then merged with necessary annotation data (annotation data set in the tile) by the display merging section 46, and finally supplied to the display device 60. This allows for the image of the new viewpoint to be displayed (S821). It should be noted, however, that, at this time, the image data (tile) deleted by the optimization may be part of the requested image. A description will be given later of this case.

[3. Operation for Optimization of Specimen Image Data Groups]

A detailed description will be given next of the optimization of specimen image data groups performed by the image optimization/deletion response section 36 of the server device 30. Image data can be deleted for optimization by one of the following:

First method: Delete image data with a predetermined resolution or higher if no annotation is set in specimen image data groups Second method: Delete tiles other than that with an annotation of all the image data with a predetermined resolution or higher Third method: Delete image data in the layers with a resolution higher than that of the layer with an annotation set in image data A description will be given below of each of the optimization methods.

Figure 11:
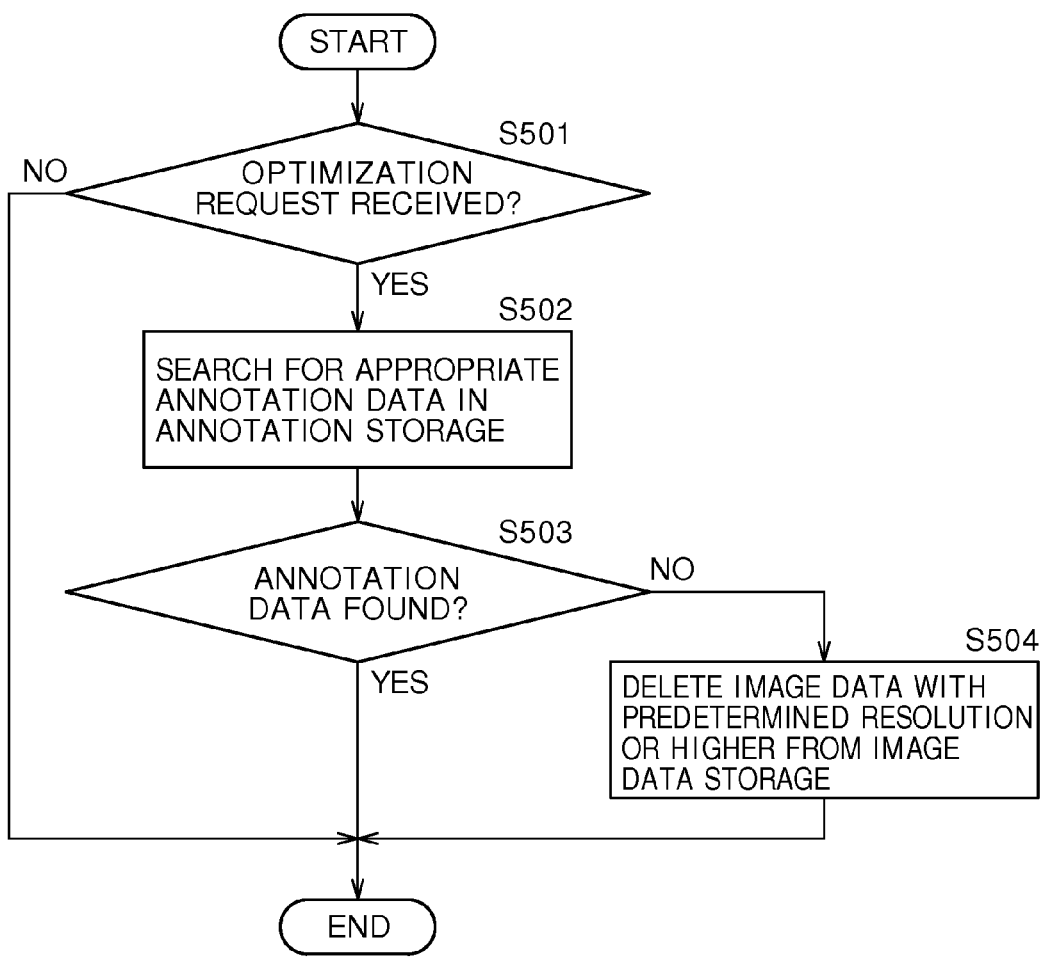
FIG. 11 is a flowchart illustrating a first optimization method of specimen image data groups.

FIG. 11 is a flowchart of the first optimization method of specimen image data groups. When the image optimization/deletion response section 36 receives an optimization request from the viewer device 40 (Yes in step S501), the same section 36 searches for annotation data associated with the specimen title included in the optimization request in the annotation storage 33 (step S502). If there is no appropriate annotation data (No in step S503), the image optimization/deletion response section 36 determines that the image data with a predetermined resolution or higher is unnecessary, thus deleting the image data from the image data storage 32 (step S504). On the other hand, when annotation data associated with the specimen title included in the optimization request is found in the annotation storage 33 (Yes in step S503), the image optimization/deletion response section 36 terminates the optimization without doing anything.

FIG. 12 is a diagram illustrating an example of optimization using the first method.

We assume, for example, that no annotation is set in any tile in any layer of the image pyramid structure made up of three layers. In method 1, if no annotation is set in any layer, the image optimization/deletion response section 36 determines that the image data with a predetermined resolution or higher is unnecessary, thus deleting the image data from the image data storage 32. This example illustrates a case in which all the image data with the resolution of layer 3 (original image) or higher is deleted. The resolution of the image data to be deleted may be specified to change the resolution. Alternatively, the image data subject to deletion may be selected by specifying a layer rather than a resolution.

Figure 13:
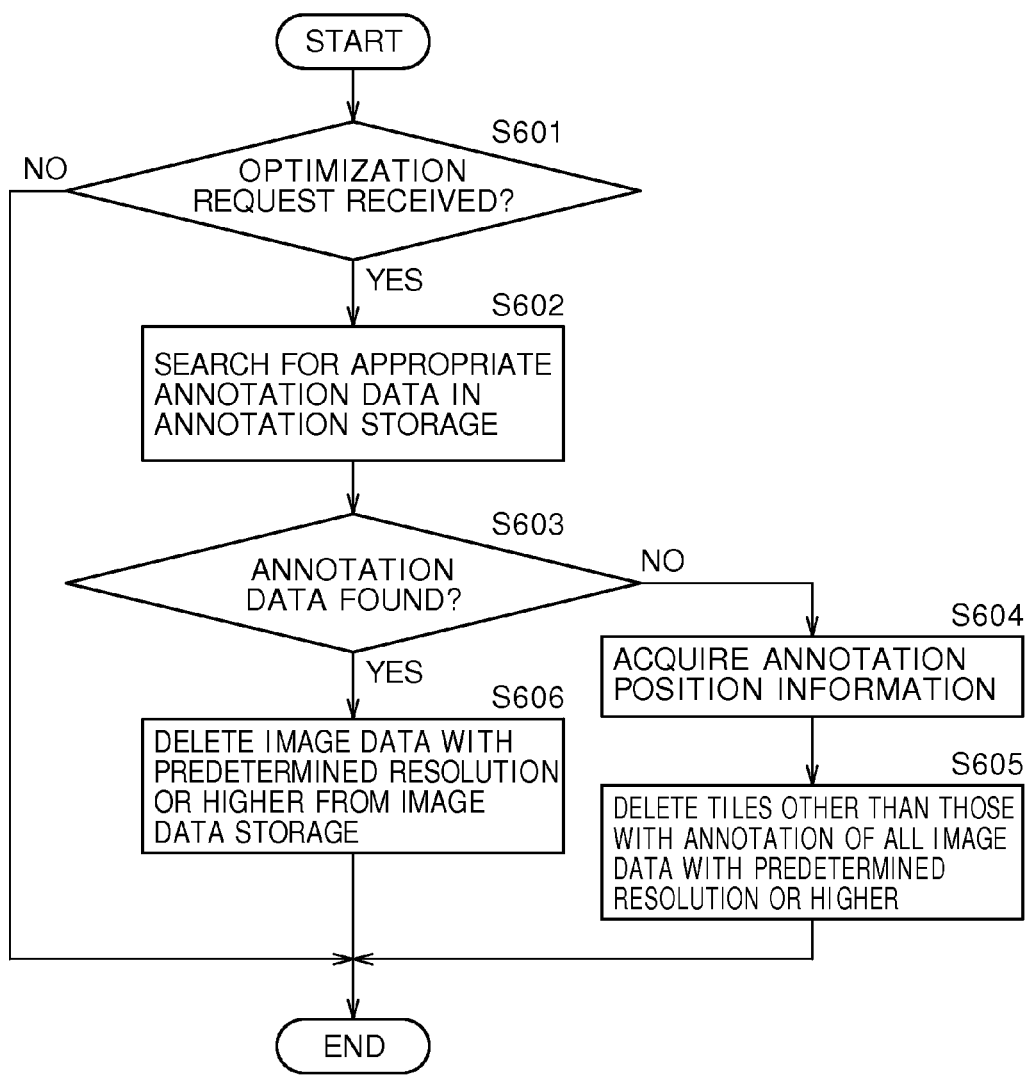
FIG. 13 is a flowchart illustrating a second optimization method of specimen image data groups.

FIG. 13 is a flowchart of the second optimization method. When the image optimization/deletion response section 36 receives an optimization request from the viewer device 40 (Yes in step S601), the same section 36 searches for annotation data associated with the specimen title included in the optimization request in the annotation storage 33 (step S602). When there is appropriate annotation data (Yes in step S603), the image optimization/deletion response section 36 acquires annotation position information, i.e., the layer in which an annotation is set and the annotation position in the coordinate space of the image in the layer in question (step S604). The image optimization/deletion response section 36 calculates the ID of the tile including the annotation based on the acquired annotation position information and determines that tiles other than that with the annotation of all the image data in the layers with a predetermined resolution or higher are unnecessary, thus deleting the image data from the image data storage 32 (step S605). If there is no annotation data associated with the specimen title included in the optimization request in the annotation storage 33 (No in step S603), the image optimization/deletion response section 36 determines that the image data with a predetermined resolution or higher is unnecessary, thus deleting the image data from the image data storage 32 (step S606).

FIG. 14 is a diagram illustrating an example of optimization using the second method.

Assuming, for example, that annotations A1 and A2 are included, one in each of two tiles in layer 3 (original image), in the image pyramid structure made up of three layers, we consider a case in which the image data in layer 3 (original image) or below is subject to deletion for optimization. In this case, the image optimization/deletion response section 36 determines, according to the second method, that, of the image data in layer 3 (original image), those tiles other than the tiles including the annotations A1 and A2 (tiles with tile IDs of '8' and '9') are unnecessary, thus deleting the image data from the image data storage 32. The same holds true when the image data in layer 2 or below is subject to deletion.

Figure 15:
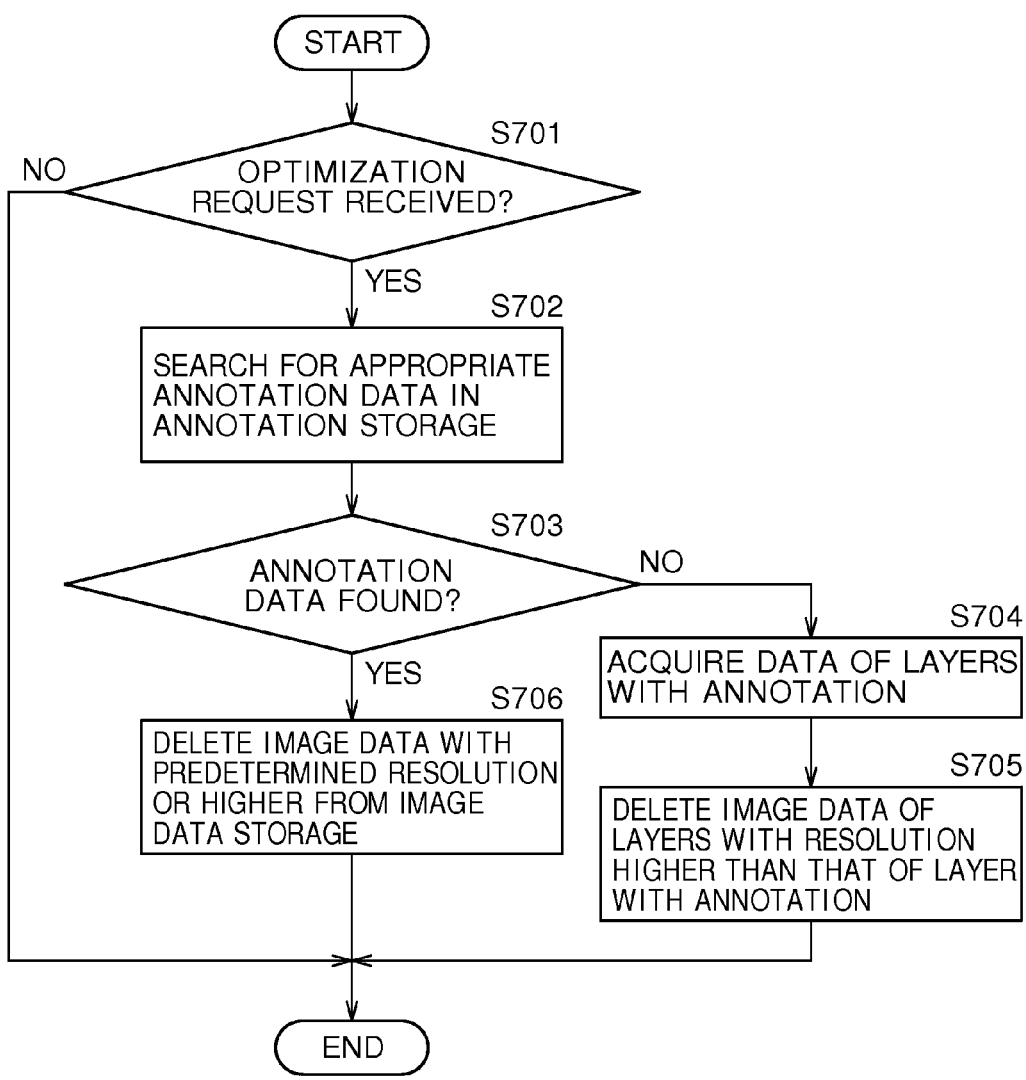
FIG. 15 is a flowchart illustrating a third optimization method of specimen image data groups.

FIG. 15 is a flowchart of the third optimization method. When the image optimization/deletion response section 36 receives an optimization request from the viewer device 40 (Yes in step S701), the same section 36 searches for annotation data associated with the specimen title included in the optimization request in the annotation storage 33 (step S702). When there is appropriate annotation data (Yes in step S703), the image optimization/deletion response section 36 acquires, of the annotation data, the data in the layer with annotations (step S704). The same section 36 determines that the image data in the layers with a resolution higher than that of the layer with annotations is unnecessary, thus deleting the image data from the image data storage 32 (step S705). When there is no appropriate annotation data associated with the specimen title included in the optimization request in the annotation storage 33 (No in step S703), the image optimization/deletion response section 36 determines that the image data with a predetermined resolution or higher is unnecessary, thus deleting the image data from the image data storage 32 (step S706).

FIG. 16 is a diagram illustrating an example of optimization using the third method.

We assume, for example, that an annotation A3 is included in layer 2 in the image pyramid structure made up of three layers. In this case, the image optimization/deletion response section 36 determines, according to the third method, that the image data in the layer with a resolution higher than that of layer 2, i.e., the image data in layer 3 (original image), is unnecessary, thus deleting the image data from the image data storage 32.

[4. Operation for Display of the Image Including the Tile Deleted for Optimization]

As described earlier, it is likely that an image area including a deleted tile deleted by optimization may be displayed. In this case, there is a problem as to how the area corresponding to the deleted tile should be displayed. The following are possible remedies:

First method: Display the area of the deleted tile in black

Second method: Generate a dummy tile from image data in a different layer and display the dummy tile A description will be given here of a case in which the second method is used.

Figure 20:
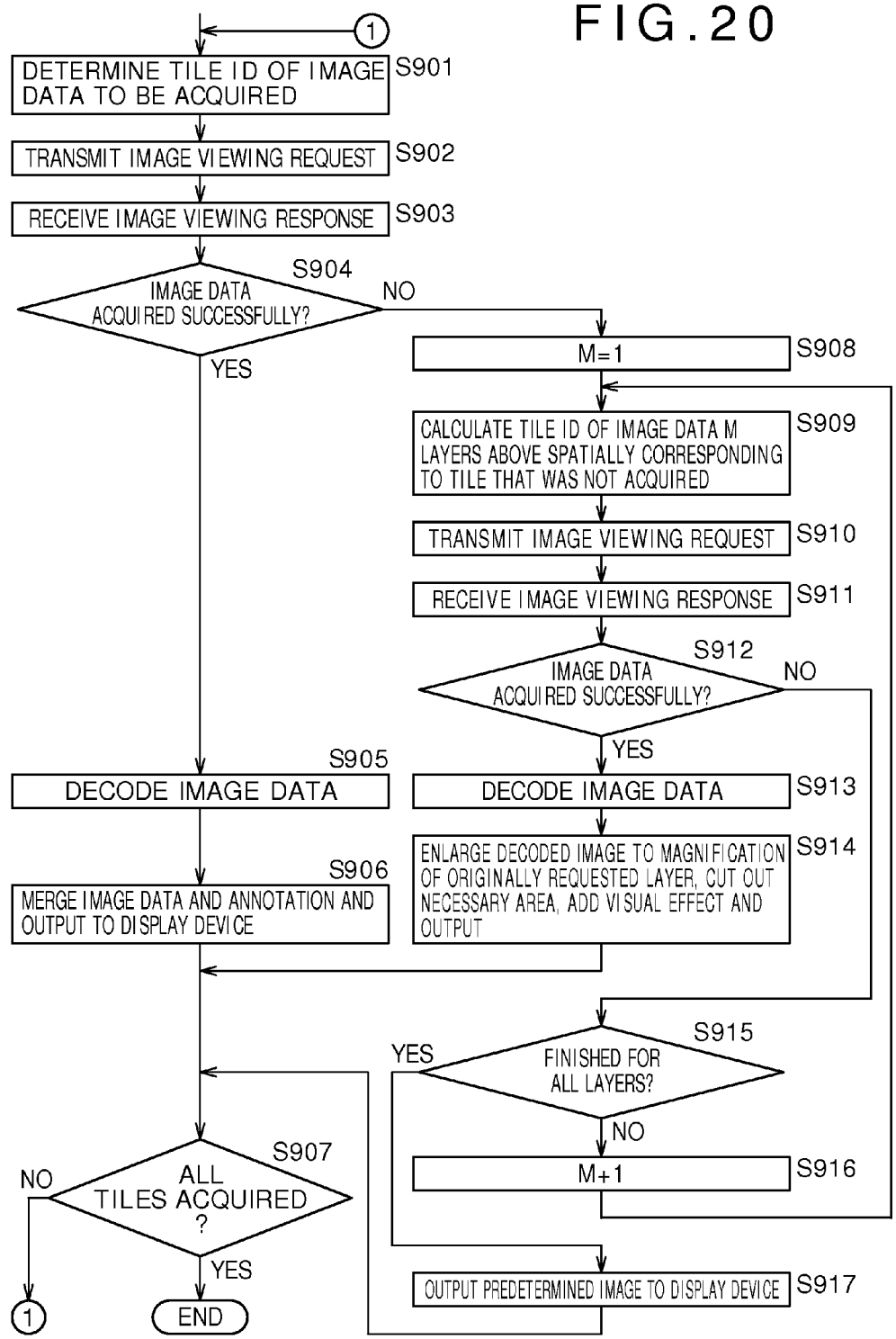
FIG. 20 is a flowchart illustrating the operation of the viewer device when image areas including tiles deleted by optimization are displayed using image data in other layer.

FIG. 20 is a flowchart illustrating the operation of the viewer device 40 when image areas including tiles deleted by optimization are displayed using image data in other layer.

After determining the tile ID of the image data to be acquired (step S901), the image data acquisition section 43 of the viewer device 40 generates an image viewing request including the tile ID, transmitting the request to the server device 30 (step S902).

In response to an imaging viewing request, the server device 30 transmits, to the viewer device 40, image data associated with the tile ID included in the imaging viewing request as an imaging viewing response when such data is stored in the image data storage 32. If such data is not stored in the image data storage 32, the server device 30 transmits, to the viewer device 40, information to the effect that the image data is not stored as an imaging viewing response.

When the image data acquisition section 43 of the viewer device 40 receives an imaging viewing response from the server device 30 (step S903), and when image data is included in the image viewing response (Yes in step S904), the same section 43 supplies the image data to the decoder 45 (step S905). The image data decoded by the decoder 45 is merged with associated annotation data by the display merging section 46, and supplied to the display device 60 (step S906).

On the other hand, if no image data is included in the image viewing response (No in step S904) because the tile deleted by optimization is the image to be acquired, the image data acquisition section 43 initializes a variable M to '1' (step S908), thus calculating the tile ID of the image data tile in the immediately upper layer positionally corresponding to the tile that was not acquired (step S909). The variable M indicates how many layers above the layer of the requested tile the image data should be acquired. Then, the image data acquisition section 43 generates an image viewing request including the tile ID, transmitting the request to the server device 30 (step S910). When the image data acquisition section 43 of the viewer device 40 successfully acquires substitute image data from the server device 30 (step S911 and Yes in step 912), the same section 43 supplies the image data to the decoder 45 (step S913). The image data decoded by the decoder 45 is supplied to the display merging section 46. The same section 46 enlarges the decoded image to the magnification ratio of the image data in the originally requested layer, cuts out the image in the necessary area, adds a predetermined visual effect as dummy tiles, and then outputs the image to the display device 60 (step S914).

Figure 21:
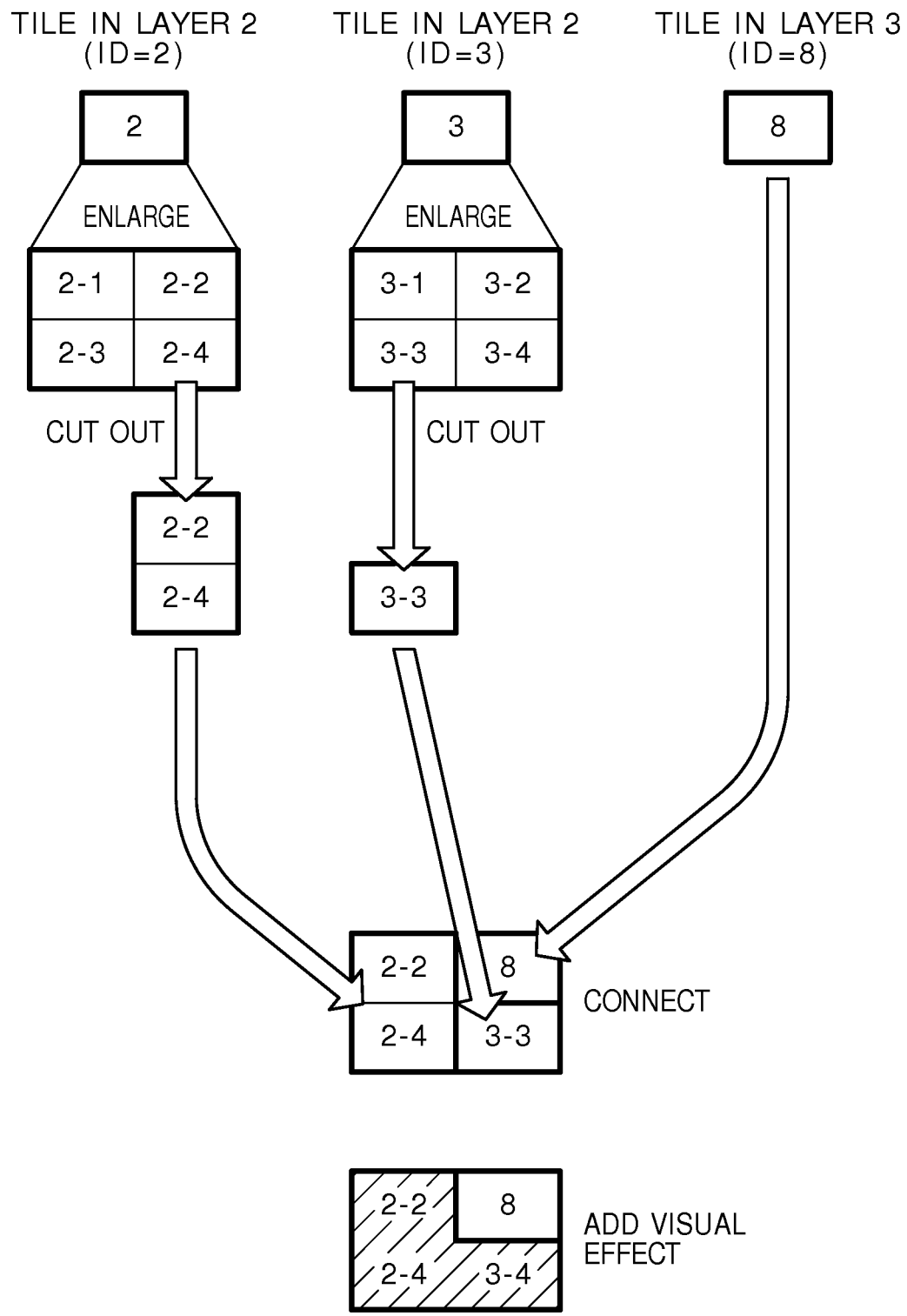
FIG. 21 is a diagram illustrating the outline of a process adapted to display an image using dummy tiles.

For example, we consider a case in FIG. 14 in which the tiles to be viewed are the tiles with IDs of '7,' '8,' '11' and '12' in layer 3 (original image). We assume that the annotation A1 is set in the tile with an ID of '8' in layer 3 (original image), and that the three tiles with IDs of '7,' '11' and '12' have been deleted by optimization. FIG. 21 is a diagram illustrating the outline of a process adapted to display the image using dummy tiles.

The image data acquisition section 43 acquires two tiles, i.e., the tile with an ID of '2' in layer 2 spatially corresponding to the two tiles with IDs of '7' and '11' and the tile with an ID of '3' in layer 2 spatially corresponding to the tile with an ID of '12' as illustrated in FIG. 14. The display merging section 46 enlarges each of the tiles with IDs of '2' and '3' two-fold as illustrated in FIG. 21. Next, the display merging section 46 divides each piece of the enlarged image data into four equal parts. Then, the same section 46 cuts out two pieces of image data 2-2 and 2-4 in the two right-hand areas of the enlarged image of the tile with an ID of '2' for use as dummy tiles of the tiles with IDs of '7' and '11' in layer 3 (original image) to be viewed. Further, the same section 46 cuts out a piece of image data 3-3 in the bottom left area of the enlarged image of the tile with an ID of '3' for use as a dummy tile of the tile with an ID of '12' in layer 3 (original image) to be viewed. Next, the display merging section 46 uniformly subjects the cut-out pieces of image data 2-2, 2-4 and 3-3 to image processing to add a predetermined visual effect as dummy tiles. Then, the same section 46 connects together the cut-out pieces of image data 2-2, 2-4 and 3-3 and the tile with an ID of '8' in layer 3 (original image) with the annotation A1 into a single piece of image data.

The process adapted to uniformly reduce the luminosity of the image data by a given ratio is an example of a visual effect added as dummy tiles. However, the process performed as a visual effect is not limited thereto, and any process is acceptable so long as the process allows for the user to visually identify the dummy tiles as such.

If the image data acquisition section 43 of the viewer device 40 fails to acquire image data tiles in the immediately upper layer (No in step S912), the same section 43 increments the value M (step S915) and attempts to acquire the image data tiles in the further upper layer. Finally, if the image data acquisition section 43 fails to acquire image data that can generate a dummy tile from any layer (Yes in step S916), the display merging section 46 generates a predetermined image adapted to fill the tiles, thus outputting the image to the display device 60 (step S917). A predetermined image may be, for example, a black image.

As described above, in the present embodiment, the image optimization/deletion response section 36 of the server device 30 determines, based on the annotations set in the image data and on a layer-by-layer or tile-by-tile basis, whether image data is unnecessary, thus deleting the image data from the image data storage 32. Here, image data with an annotation is that which drew attention of the image observer at least once. Therefore, it can be said that this data is highly valuable in terms of informativeness. Therefore, this data is excluded from data subject to deletion for optimization. In contrast, it can be said that image data with no annotation is relatively low in value in terms of informativeness. Therefore, this data is subject to deletion for optimization. Therefore, the present disclosure allows for effective downsizing of image data layered at different resolutions without reducing the informativeness of the image data, thus contributing to substantially improved capacity utilization efficiency of the device adapted to store image data and ensuring reduced operation cost.

Further, the present embodiment can reproduce and display a tile, deleted by optimization, in a dummy manner, thus providing an image to be viewed less unnatural than the image devoid of the deleted tile. Further, the tile deleted by optimization is likely to be image data relatively low in value in terms of informativeness. Therefore, compensating for the deleted tile with a dummy tile generated in a dummy manner from a spatially corresponding tile in other layer is not detrimental at all to the observation.

[Relationship Between the Microscopic System 100 According to the First Embodiment and the Information Processor According to the Present Disclosure]

In the first embodiment, the microscopic system 100 includes the microscopic device 10, control device 20, server device 30 and viewer device 40. However, each of the control device 20, server device 30 and viewer device 40 is not necessarily implemented as an individual device. For example, the control device 20, server device 30 and viewer device 40 may be combined into a single computer-based information processor. Alternatively, the server device 30 and viewer device 40 may be combined into a single information processor. Still alternatively, the control device 20 and server device 30 may be combined into a single information processor.

[Hardware Configuration of the Control Device 20, Server Device 30 and Viewer Device 40]

A description will be given next of the hardware configuration of the control device 20, server device 30 and viewer device 40. Each of the control device 20, server device 30 and viewer device 40 has typical computer hardware.

Figure 22:
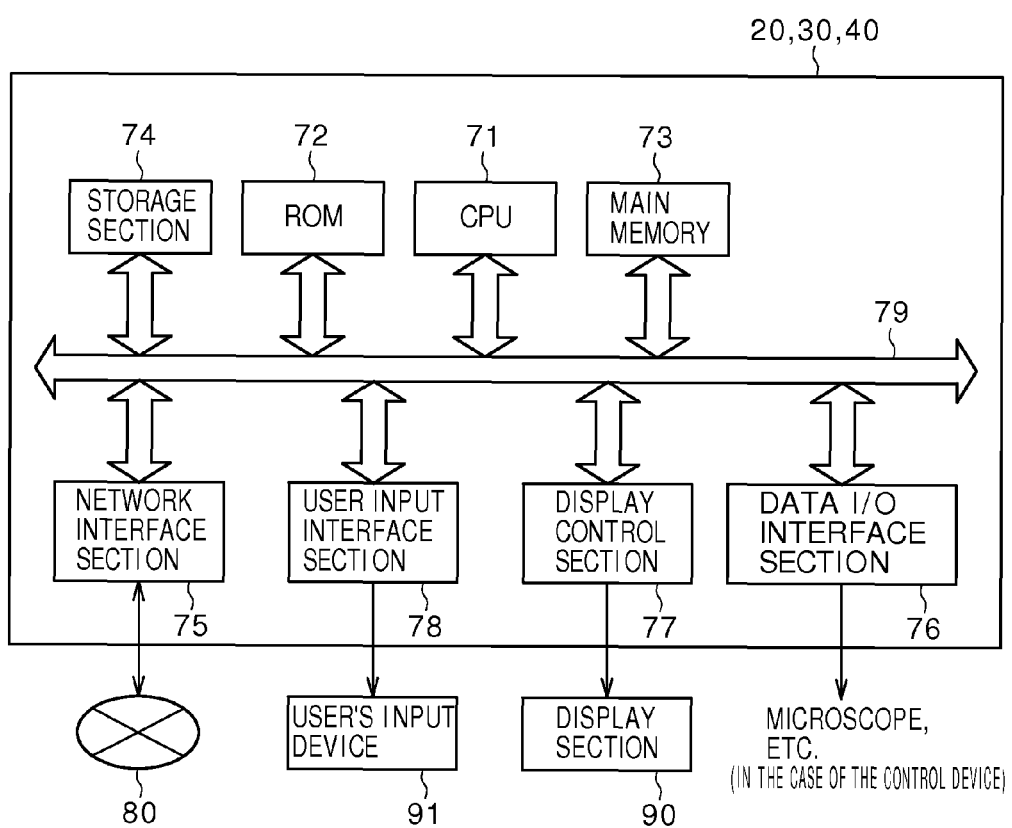
FIG. 22 is a diagram illustrating the hardware configuration of a computer.

FIG. 22 is a diagram illustrating the hardware configuration of the computer used in each of the control device 20, server device 30 and viewer device 40.

As illustrated in FIG. 22, the computer includes, for example, a CPU 71, ROM 72, main memory 73, storage section 74, network interface section 75, data I/O interface section 76, display control section 77, user input interface section 78 and system bus 79.

The ROM 72 stores programs executed by the CPU 71, various fixed data and other information.

The main memory 73 is used as a work area for arithmetic operations performed by the CPU 71.

The storage section 74 is designed to store image data and other data as user data. More specifically, the same section 74 is a large-capacity rewritable storage device such as HDD or SSD (Solid State Drive).

The network interface section 75 handles wired and wireless connections with a network 80 such as the Internet or a local area network.

The data I/O interface section 76 is used for exchange of various data with external device (e.g., microscopic device 10).

The display control section 77 generates display data to be output to a display device 90.

The user input interface section 78 handles inputs from an input device 91 of the user such as a mouse, keyboard or controller.

The CPU (Central Processing Unit) 71 can exercise control and perform arithmetic operations in a variety of manners according to the programs stored in the ROM 72.

It is needless to say that the present disclosure is not limited to the above-described embodiment but may be modified in various ways without departing from the spirit of the present disclosure.

MODIFICATION EXAMPLE

There is not necessarily a single server device. Each process may be distributed among two or more server devices. Alternatively, there may be two or more viewer devices connected to the server device. In this case, it is possible for a plurality of observers to observe the same specimen image at the same time by transmitting the same image viewing request from the viewer devices to the server device, thus contributing to improved diagnostic efficiency. On the other hand, if two or more viewer devices are connected to the server device, it is preferred to introduce an arrangement adapted to manage the rights to transmit an optimization request.

The viewer device 40 may integrally include the controller 50 or display device 60.

The present disclosure contains subject matter related to that disclosed in Japanese Priority Patent Application JP 2010-287247 filed in the Japan Patent Office on Dec. 24, 2010, the entire content of which is hereby incorporated by reference.

What is claimed is:
1. An information processor, comprising: one or more processors operable to:
store a first piece of first image data that has a first resolution and at least one second piece of second image data as layer-by-layer image data for a specimen, wherein the at least one second piece of second image data is obtained by a spatial compression on the first piece of first image data at different magnification ratios;
acquire one of the first image data or the second image data in units of a second resolution from the stored layer-by-layer image data to display the acquired one of the first image data or the second image data on a display device, wherein each of the units of the second resolution corresponds to a tile that comprises a plurality of pixels:
set annotations in the units of the second resolution based on an instruction from a user, wherein the annotations are set by an area marked as a suspected lesion part in the displayed image data;
acquire annotation positional information of a first layer of the layer-by-layer image data in which the annotations are set and the annotation position in coordinate space of the displayed one of the first image data or the second image data in the first layer for each unit of the second resolution which comprises the set annotations; and delete at least one tile, other than a first tile with the annotations, of all the corresponding tiles of the units in the first layer in which annotation is set to delete the one of the first image data or the second image data of a plurality of layers in the layer-by-layer image data with the first resolution higher than that of the first layer in which the annotations are set, wherein the at least one tile has the second resolution equal to or higher than a determined resolution.

2. The information processor according to claim 1, wherein the at least one second piece of second image data is image data obtained by spatial compression of the first piece of first image data at magnification ratios of $1/2$, $1/2^2$, $1/2^3$ and so on down to $1/2^N$ (where N is a constant equal to or greater than 1).

3. The information processor according to claim 1, wherein based on a lack of annotation in at least one unit of the units of the second resolution in the layer-by-layer image data for the specimen, the one or more processors are further operable to delete the at least one of the second resolution, in a second layer of the layer-by-layer image data with a resolution equal to or higher than the determined resolution.

4. The information processor according to claim 1, wherein the one or more processors are further operable to:
based on a deletion of the at least one tile that corresponds to one of the first image data or the second image data to be displayed, acquire a second tile from a second layer of the layer-by-layer image data, wherein the second tile spatially corresponds to the deleted at least one tile; and
generate a dummy tile, of the deleted tile, from the acquired second tile.

5. The information processor according to claim 4, wherein the one or more processors are further operable to add a visual feature to the generated dummy tile such that the dummy tile is identifiable from a normal tile.

6. An image data optimization method, comprising:
in one or more processors:
storing a first piece of first image data that has a first resolution and at least one second piece of second image data as layer-by-layer image data for a specimen, wherein the at least one second piece of second image data is obtained by spatially compressing the first piece of first image data at different magnification ratios;
acquiring one of the first image data or the second image data in units of a second resolution from the stored layer-by-layer image data to display the acquired one of the first image data or the second image data on a display device, wherein each of the units of the second resolution corresponds to a tile that comprises a plurality of pixels;
setting annotations in the units of the second resolution based on an instruction from a user;
acquiring annotation positional information of a layer of the layer-by-layer image data in which the annotations are set and the annotation position in coordinate space of the displayed one of the first image data or the second image data in the layer for each unit of the second resolution which comprises the set annotations; and
deleting at least one tile, other than a first tile with the annotations, of all the corresponding tiles of the units in the first layer in which annotation is set to delete the one of the first image data or the second image data of a plurality of layers in the layer-by-layer image data with the first resolution higher than that of the layer in which the annotations are set, wherein the at least one tile has the second resolution equal to or higher than a determined resolution.

7. A non-transitory computer-readable medium having stored thereon, computer-executable instructions for causing a computer to execute operations, the operations comprising:
storing a first piece of first image data that has a first resolution and at least one second piece of second image data as layer-by-layer image data for a specimen, wherein the at least one second piece of second image data is obtained by spatially compressing the first piece of first image data at different magnification ratios;
acquiring one of the first image data or the second image data in units of a second resolution from the stored layer-by-layer image data to display the acquired one of the first image data or the second image data on a display device, wherein each of the units of the second resolution corresponds to a tile that comprises a plurality of pixels;
setting annotations in the units of the second resolution based on an instruction from a user, wherein the annotations are set by marking an area suspected as a lesion part in the displayed image data;
acquiring annotation positional information of a layer of the layer-by-layer image data in which the annotations are set and the annotation position in coordinate space of the displayed one of the first image data or the second image data in the layer for each unit of the second resolution which comprises the set annotations; and
deleting at least one tile, other than a first tile with the annotations, of all the corresponding tiles of the units in the first layer in which annotation is set to delete the one of the first image data or the second image data of a plurality of layers in the layer-by-layer image data with the first resolution higher than that of the layer in which the annotations are set, wherein the at least one tile has the second resolution equal to or higher than a determined resolution.

* * * * *